United States Patent
Lickert et al.

(10) Patent No.: US 11,999,776 B2
(45) Date of Patent: Jun. 4, 2024

(54) IGFR-LIKE 2 RECEPTOR AND USES THEREOF

(71) Applicant: Helmholtz Zentrum München—Deutsches Forschungszentrum Für Gesundheit Und Umwelt (GmbH), Neuherberg (DE)

(72) Inventors: Heiko Lickert, Munich (DE); Ünal Coskun, Dresden (DE); Sarah Homberg, Eching (DE)

(73) Assignee: Helmholtz Zentrum München—Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 85 days.

(21) Appl. No.: 17/412,066

(22) Filed: Aug. 25, 2021

(65) Prior Publication Data

US 2022/0048974 A1 Feb. 17, 2022

Related U.S. Application Data

(63) Continuation-in-part of application No. 16/481,781, filed as application No. PCT/EP2018/052267 on Jan. 30, 2018, now abandoned.

(30) Foreign Application Priority Data

Jan. 30, 2017 (EP) ..................... 17153782
Mar. 16, 2017 (LU) ..................... 100143

(51) Int. Cl.
C07K 14/71 (2006.01)
C07K 16/28 (2006.01)
G01N 33/50 (2006.01)

(52) U.S. Cl.
CPC .......... *C07K 14/71* (2013.01); *C07K 16/2863* (2013.01); *G01N 33/5041* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| 5,382,574 A | 1/1995 | Jorgensen |
| 9,061,059 B2 | 6/2015 | Chakraborty et al. |
| 2003/0134788 A1* | 7/2003 | Baker .................. C12Q 1/6837 514/18.9 |
| 2007/0082337 A1 | 4/2007 | Sorek et al. |

FOREIGN PATENT DOCUMENTS

| WO | WO 2010/048497 | 4/2010 |
| WO | WO 2015/156470 A1 | 10/2015 |

OTHER PUBLICATIONS

Jain et al., Nature Metabolism, 4:1097-1108, Sep. 2022.*
Ansarullah et al., Nature, 590:326-331, Feb. 2021; https://doi.org/10.1038/s41586-021-032225-8.*
Database Accession No. AYE25596, "Human Alzheimer's Disease Related Coding Sequence Seq ID:643," dated Sep. 2, 2010, 2 pages.
Database Accession No. AYE25597, "Human Alzheimer's Disease Related Polypeptide, Seq ID:644," dated Sep. 2, 2010, 1 page.
King, (2012) British Journal of Pharmacology, 166:877-894.

\* cited by examiner

*Primary Examiner* — Marianne P Allen
(74) *Attorney, Agent, or Firm* — Kagan Binder, PLLC

(57) ABSTRACT

The present invention provides a novel IGFR-like receptor 2 and antagonists and agonists for targeting said receptor. Said antagonists and agonists are envisaged for use as a medicament, and in particular for treatment of cancer or diabetes.

5 Claims, 17 Drawing Sheets

Specification includes a Sequence Listing.

Figure 7 (SEQ ID NO: 1 (IGFR-I 2))

```
ATGCTGTTCCGCGCCCGGGGGCCGGTACGGGGCAGGGGCTGGGGGCGGCCGGCGGAGGCTCCCCGCCGCGGGCGCTCGCCGCC
CTGGAGCCCCGCCTGGATTTGCTGCTGGGCGCTCGCCGGCTGCCAGGCGGCCTGGGCTGGGGACCTGCCCTCCTCCTCCAGCC
GCCCGCTTCCTCCTTGCCAGGAGAAAGATTATCACTTTGAATATACGGAATGTGATAGCAGTGGCTCCAGGTGGAGAGTTGCC
ATTCAAATTCTGCAGTGGACTGCTCTGGCCTGCCTGACCTAGTGAGAGGCAAAGAATGCACTTTCTCCTGTGCTTCTGGAGA
GTATCTAGAAATGAAGAACCAGGTATGCAGTAAGTGTGGTGAAGGCACCTATTCCTTGGGCAGTGGCATCAAATTTGATGAAT
GGGATGAATTGCCGGCAGGATTTTCTAACATCGCAACATTCATGGACACTGTGGTGGGCCCTTCTGACAGCAGGCCAGACGGC
TGTAACAACTCTTCTTGGATCCTCGTGGAAACTACATAGAATCTAATCGTGATGACTGTACGTGTCTTTGATCTATGCTGT
GCACCTTAAGAAGTCAGGCTATGTCTTCTTTGAGTACCAGTATGTCGACAACAACATCTTCTTGAGTTCTTATTCAAAATG
ATCAGTGCCAGGAGATGGACACCACCACTGACAAGTGGGTAAAACTTACAGACAATGGAGAATGGGCTCTCATTCTGTAATG
CTGAAATCAGGCACAAACATACTCTACTGGAGAACTACAGGCATCTTATGGGTTCTAAGGCGGTCAAGCCTGTGCTGGTAAA
AAATATCACAATTGAAGGGGTGGCGTACACATCAGAATGTTTTCCTTGCAAGCCAGGCACATTCAGCAACAAACCAGGTTCAT
TCAACTGCCAGGTGTGTCCCAGAAACACCTATTCTGAGAAAGGAGCCAAAGAATGTATAAGGTGTAAAGACGACTCTCAATTT
TCAGAGGAAGGATCCAGTGAGTGTACAGAGCGCCCTCCTGTACCACAAAAGACTATTTCCAGATCCATACTCCATGTGATGA
AGAAGGAAAGACACAGATAATGTACAAGTGGATAGAGCCCAAAATCTGCCGGGAGGATCTCACAGATGCTATTAGATTGCCCC
CTTCTGGAGAGAAGAAGGATTGTCCGCCTTGCAACCCTGGATTTTATAACAATGGATCATCTTCTTGCCATCCCTGTCCTCCT
GGAACATTTTCAGATGGAACCAAAGAATGTAGACCATGTCCAGCAGGAACGGAGCCTGCACTTGGCTTCAATATAAATGGTG
GAATGTCCTTCCTGGCAACATGAAAACTTCCTGCTTCAATGTTGGGAATTCAAAGTGCGATGGAATGAATGGTTGGGAGGTGG
CTGGAGATCATATCCAGAGTGGGGCTGGAGGTTCTGACAATGATTACCTGATCTTAAACTTGCATATCCCAGGATTTAAACCA
CTAACATCTATGACTGGAGCCACGGGTTCTGAACTAGGAAGAATAACATTTGTCTTTGAGACCCTCGTTCAGCTGACTGTGT
TTTGTACTTCATGGTGGATATTAATAGAAAAAGTACAAATGTGGTAGAATCGTGGGGTGGAACCAAAGAAAAACAAGCTTACA
CCCATATCATCTTCAAGAATGCAACTTTTACATTTACATGGGCATTCCAGAGAACTAATCAGGGTCAAGATAATAGACGGTTC
ATCAATGACATGGTGAAGATTTATTCTATCACAGCCACTAATGCAGTTGATGGGTGGCGTCCTCATGCCGTGCCTGTGCCCT
CGCTTCTGAACAGTCGGGTTCATCGTGTGTCCCTGCCCTCCAGGCCACTACATTGAGAAAGAAACCAACCAGTCAAGGAAT
GTCCACCTGACACCTACCTGTCCATACATCAGGTCTATGGCAAAGACGCTTGATTCCATGCGGGCCTGGACTAAAAACAAT
CAGGACCATTCGGTTTGCTATAGTGACTGCTTTTTCTACCATGAAAAGAAAATCAGAGTTTGCACTATGACTTTAGCAACCT
CAGCAGTGTGGGCTCATTAATGAATGGCCCCAGCTTCACCTCCAAAGGAACAAAATACTTCCATTTCTTCAATATCAGTTTAT
GTGGGCATGAGGGGAAGAAGATGGCTCTCTGTACCAACAATATAACAGACTTTACAGTAAAAGAAATAGTGGCAGGGTCAGAT
GATTACACAAATTGGTAGGGGCATTTGTATGCCAGTCAACAATTATTCCTTCTGAAAGTAAGGGTTCCGAGCAGCCTTATC
ATCACAATCCATCATTCTGGCAGATACATTCATAGGAGTCACAGTTGAAACCACATTGAAAAATATTAATATAAAAGAAGATA
TGTTCCCAGTTCCAACAAGCCAAATACCAGATGTGCATTTCTTTTATAAGTCTTCTACAGCAACAACATCTTGTATTAATGGC
CGATCAACTGCTGTGAAAATGAGGTGTAATCCTACTAAATCTGGAGCAGGAGTGATTTCAGTCCCCAGCAAGTGCCCAGCAGG
TACCTGTGATGGGTGTACGTTCTATTTCCTGTGGGAGAGTGCTGAAGCTTGCCCTCTGTACGGAGCATGACTTCCATGAGA
TTGAGGGAGCCTGCAAGAGAGGATTTCAGGAAACCTTGTATGTGTGGAATGAACCTAAATGGTGCATTAAAGGAATTTCTTTG
CCTGAGAAAAGTTGGCAACCTGTGAAACGGTTGACTTTTGGTTGAAGGTGGGAGCCGGTGTGGGAGCTTTTACTGCCGTTTT
GCTGGTGGCTCGACCTGCTACTTCTGGAAAAGAATCAAAAACTGGAATACAAATATTCCAAGTTAGTAATGACGACTAACT
CAAAAGAGTGTGAACTCCCGGCTGCAGACAGTTGTGCTATCATGGAAGGAGAAGATAATGAAGAGGAAGTTGTATATTCCAAT
AAACAGTCACTACTAGGAAAACTCAAATCTTTGGCAACCAAGGAAAAAGAAGACCATTTTGAATCTGTTCAACTGAAAACCTC
AAGATCCCCAAATATATGA
```

Figure 8 (SEQ ID NO: 2 (IGFR-I 2))

```
MLFRARGPVRGRGWGRPAEAPRRGRSPPWSPAWICCWALAGCQAAWAGDLPSSSSRPLPPCQEKDYHFEYTECDSSGSRW
RVAIPNSAVDCSGLPDPVRGKECTFSCASGEYLEMKNQVCSKCGEGTYSLGSGIKFDEWDELPAGFSNIATFMDTVVGPS
DSRPDGCNNSSWIPRGNYIESNRDDCTVSLIYAVHLKKSGYVFFEYQYVDNNIFFEFFIQNDQCQEMDTTTDKWVKLTDN
GEWGSHSVMLKSGTNILYWRTTGILMGSKAVKPVLVKNITIEGVAYTSECFPCKPGTFSNKPGSFNCQVCPRNTYSEKGA
KECIRCKDDSQFSEEGSSECTERPPCTTKDYFQIHTPCDEEGKTQIMYKWIEPKICREDLTDAIRLPPSGEKKDCPPCNP
GFYNNGSSSCHPCPPGTFSDGTKECRPCPAGTEPALGFEYKWWNVLPGNMKTSCFNVGNSKCDGMNGWEVAGDHIQSGAG
GSDNDYLILNLHIPGFKPPTSMTGATGSELGRITFVFETLCSADCVLYFMVDINRKSTNVVESWGGTKEKQAYTHIIFKN
ATFTFTWAFQRTNQGQDNRRFINDMVKIYSITATNAVDGVASSCRACALGSEQSGSSCVPCPPGHYIEKETNQCKECPPD
TYLSIHQVYGKEACIPCGPGSKNNQDHSVCYSDCFFYHEKENQSLHYDFSNLSSVGSLMNGPSFTSKGTKYFHFFNISLC
GHEGKKMALCTNNITDFTVKEIVAGSDDYTNLVGAFVCQSTIIPSESKGFRAALSSQSIILADTFIGVTVETTLKNINIK
EDMFPVPTSQIPDVHFFYKSSTAFTSCINGRSTAVKMRCNPTKSGAGVISVPSKCPAGTCDGCTFYFLWESAEACPLCTE
HDFHEIEGACKRGFQETLYVWNEPKWCIKGISLPEKKLATCETVDFWLKVGAGVGAFTAVLLVALTCYFWKKNQKLEYKY
SKLVMTTNSKECELPAADSCAIMEGEDNEEEVVYSNKQSLLGKLKSLATKEKEDHFESVQLKTSRSPNI
```

Figure 9 (SEQ ID NO: 3 (IGFR-I 1))

```
atggctgagcctgggcacagccaccatctctccgccagagtcaggggaagaactgagaggcgcatacccggctgtggcggct
gctgctctgggctgggaccgccttccaggtgacccagggaacgggacggagcttcatgcctgcaaagagtctgagtaccact
atgagtacacggcgtgtgacagcacgggttccaggtggagggtcgccgtgccgcatacccgggcctgtgcaccagcctgcct
gaccccAtcaagggcaccgagtgctccttctcctgcaacgccggggagtttctggatatgaaggaccagtcatgtaagccatg
cgctgagggccgctactccctcggcacaggcattcggtttgatgagtgggatgagctgccccatggctttgccagcctctcag
ccaacatggagctggatgacagtgctgctgagtccaccgggaactgtacttcgtccaagtgggttccccggggcgactacatc
gcctccaacacggacgaatgcacagccacactgatgtacgccgtcaacctgaagcaatctggcaccgttaacttcgaatacta
ctatccagactccagcatcatctttgagttttttcgttcagaatgaccagtgccagcccaatgcagatgactccaggtggatga
agaccacagagaaggatgggaattccacagtgtggagctaaatcgaggcaataatgtcctctattggagaaccacagccttc
tcagtatggaccaaagtacccaagcctgtgctggtgagaaacattgccataacaggggtggcctacacttcagaatgcttccc
ctgcaaacctggcacgtatgcagacaagcagggctcctctttctgcaaactttgcccagccaactcttattcaaataaaggag
aaacttcttgccaccagtgtgaccctgacaaatactcagagaaaggatcttcttcctgtaacgtgcgcccagcttgcacagac
aaagattatttctacacacacacggcctgcgatgccaacggagagacacaactcatgtacaaatgggccaagccgaaaatctg
tagcgaggaccttgaggggcagtgaagctgcctgcctctggtgtgaagaccactgcccacctgcaacccaggcttcttca
aaaccaacaacagcacctgccagccctgcccatatggttcctactccaatggctcagactgtacccgctgccctgcagggact
gaacctgctgtgggatttgaatacaaatggtggaacacgctgccacaaacatggaaacgaccgttctcagtgggatcaactt
cgagtacaagggcatgacaggctgggaggtggctggtgatcacatttacacagctgctggagcctcagacaatgacttcatga
ttctcactctggttgtgccaggatttagacctccgcagtcggtgatggcagacacagagaataaagaggtggccagaatcaca
tttgtctttgagacctctgttctgtgaactgtgagctctacttcatggtgggtgtgaattctaggaccaacactcctgtgga
gacgtggaaaggttccaaaggcaaacagtcctatacctacatcattgaggagaacactaccacgagcttcacctgggccttcc
agaggaccacttttcatgaggcaagcaggaagtacaccaatgacgttgccaagatctactccatcaatgtcaccaatgttatg
aatggtgtggcctcctactgccgtccctgtgccctagaagcctctgatgtgggctcctcctgcacctcttgtcctgctggtta
ctatattgaccgagattcaggaacctgccactcctgccccactaacacaattctgaaagcccaccagcctattggtgtccagg
cctgtgtgccctgtggtccaggaccaagaacaacaagatccactctctgtgctacaacgattgcaccttctcacgcaacact
ccgaccaggactttcaactacaacttctccgctttggcaaacactgtcactcttgctggagggccaagcttcacttccaaagg
gctgaaatacttccatcactttaccctcagtctctgtggaaaccagggtaggaaaatgtctgtgtgcaccgacaatgtcactg
acctccggattcctgagggtgagtcagggttctccaaatctatcacagcctacgtctgcaggcagtcatcatcccccagag
gtgacaggctacaaggccggggtttcctcacagcctgtcagccttgctgatcgacttattggggtgacaacagatatgactct
ggatggaatcacctcccagctgaacttttccacctggagtccttgggaataccggacgtgatcttcttttataggtccaatg
atgtgacccagtcctgcagttctgggagatcaaccaccatccgcgtcaggtgcagtccacagaaaactgtccctggaagtttg
ctgctgccaggaacgtgctcggatgggacctgtgatggctgcaacttccacttcctgtgggagagcgcggctgcttgcccgct
ctgctcagtggctgactaccatgctatcgtcagcagctgtgtggctgggatccagaagactacttacgtgtggcgagaaccca
agctatgctctggtggcatttctctgctgagcagagagtcaccatctgcaaaaccatagatttctggctgaaagtgggcatc
tctgcaggcacctgtactgccatcctgctcaccgtcttgacctgctacttttggaaaaagaatcaaaaactagagtacaagta
ctccaagctggtgatgaatgctactctcaaggactgtgacctgccagcagctgacagctgcgccatcatggaaggcgaggatg
tagaggacgacctcatctttaccagcaagaagtcactctttgggaagatcaaatcatttacctccaagaggactcctgatgga
tttgactcagtgccgctgaagacatcctcaggaggcctagacatggacctgtga
```

Figure 10 (SEQ ID NO: 4 (IGFR-I1))

MAEPGHSHHLSARVRGRTERRIPRLWRLLLWAGTAFQVTQGTGPELHACKESEYHYEYTACDSTGSRWRVAVPHTPGLCT
SLPDPIKGTECSFSCNAGEFLDMKDQSCKPCAEGRYSLGTGIRFDEWDELPHGFASLSANMELDDSAAESTGNCTSSKWVP
RGDYIASNTDECTATLMYAVNLKQSGTVNFEYYYPDSSIIFEFFVQNDQCQPNADDSRWMKTTEKGWEFHSVELNRGNN
VLYWRTTAFSVWTKVPKPVLVRNIAITGVAYTSECFPCKPGTYADKQGSSFCKLCPANSYSNKGETSCHQCDPDKYSEKGSS
SCNVRPACTDKDYFYTHTACDANGETQLMYKWAKPKICSEDLEGAVKLPASGVKTHCPPCNPGFFKTNNSTCQPCPYGSY
SNGSDCTRCPAGTEPAVGFEYKWWNTLPTNMETTVLSGINFEYKGMTGWEVAGDHIYTAAGASDNDFMILTLVVPGFRP
PQSVMADTENKEVARITFVFETLCSVNCELYFMVGVNSRTNTPVETWKGSKGKQSYTYIIEENTTTSFTWAFQRTTFHEASR
KYTNDVAKIYSINVTNVMNGVASYCRPCALEASDVGSSCTSCPAGYYIDRDSGTCHSCPTNTILKAHQPYGVQACVPCGPG
TKNNKIHSLCYNDCTFSRNTPTRTFNYNFSALANTVTLAGGPSFTSKGLKYFHHFTLSLCGNQGRKMSVCTDNVTDLRIPEG
ESGFSKSITAYVCQAVIIPPEVTGYKAGVSSQPVSLADRLIGVTTDMTLDGITSPAELFHLESLGIPDVIFFYRSNDVTQSCSSG
RSTTIRVRCSPQKTVPGSLLLPGTCSDGTCDGCNFHFLWESAAACPLCSVADYHAIVSSCVAGIQKTTYVWREPKLCSGGISL
PEQRVTICKTIDFWLKVGISAGTCTAILLTVLTCYFWKKNQKLEYKYSKLVMNATLKDCDLPAADSCAIMEGEDVEDDLIFTS
KKSLFGKIKSFTSKRTPDGFDSVPLKTSSGGLDMDL

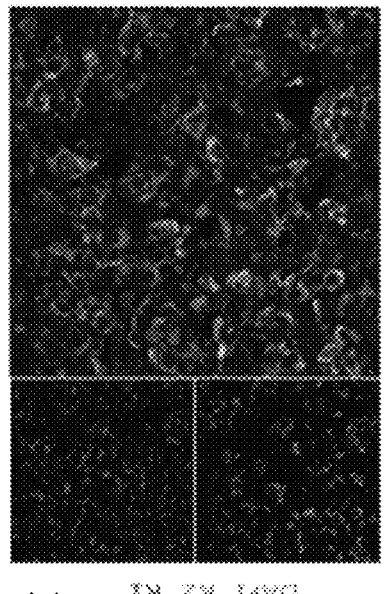
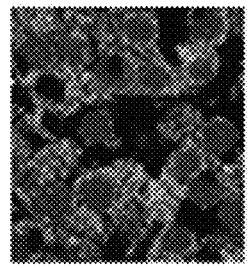
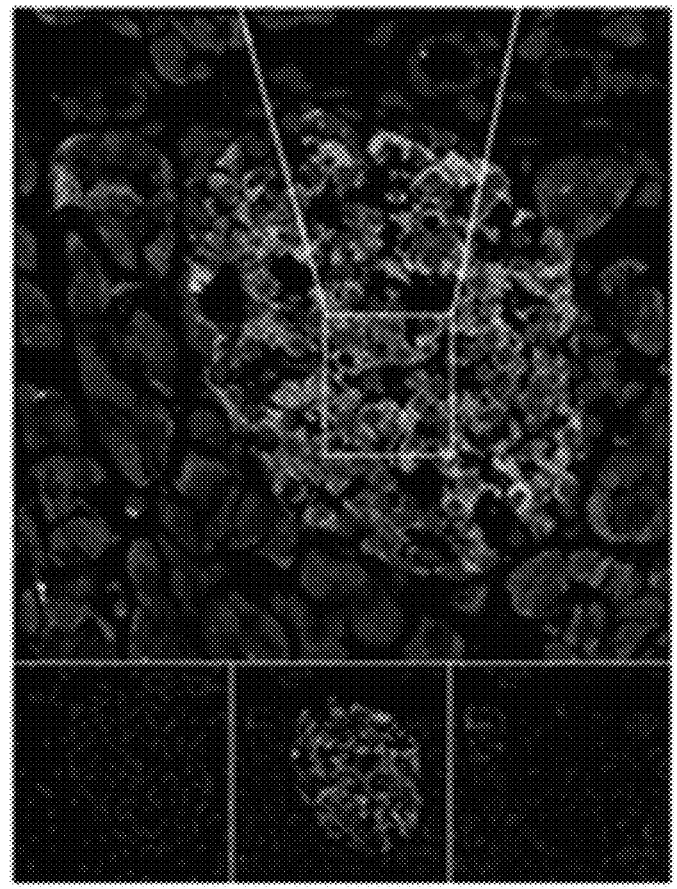
Figure 12

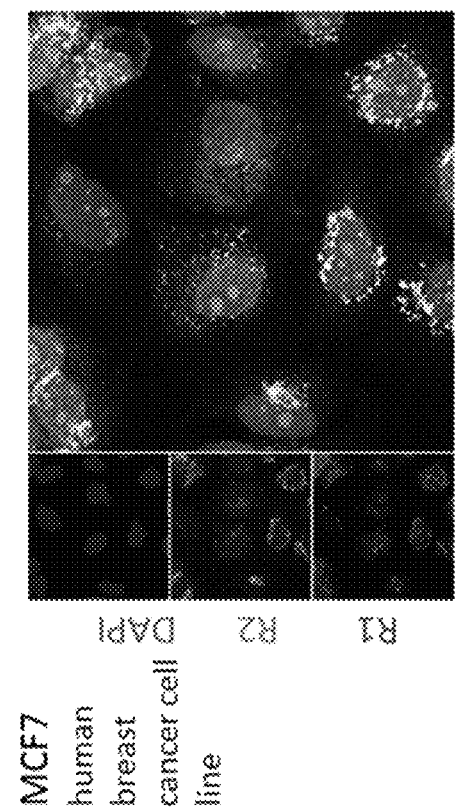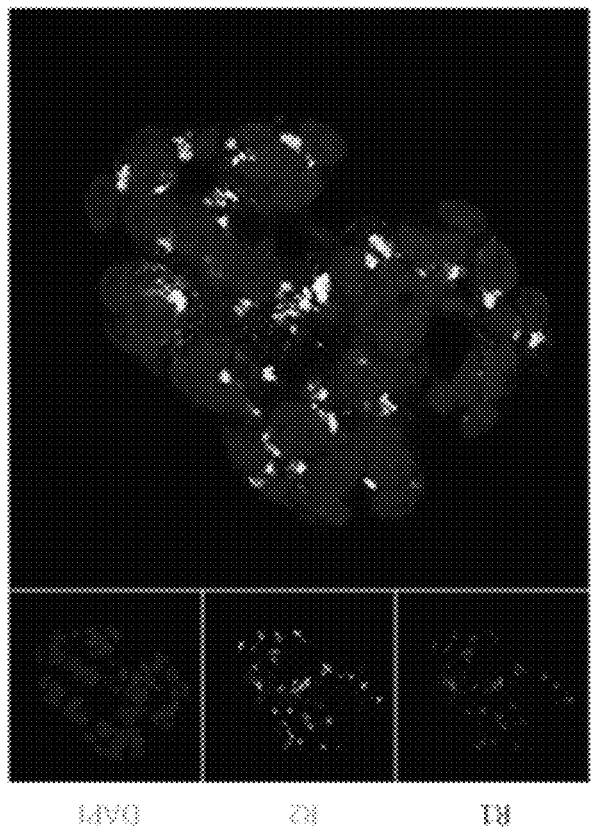
Figure 12 (cont.)

Figure 14
generation of IGFR-I 2 single and IGFR-I 1/2 double KO
CRISPR/Cas9-mediated excision of the start codon in Min6
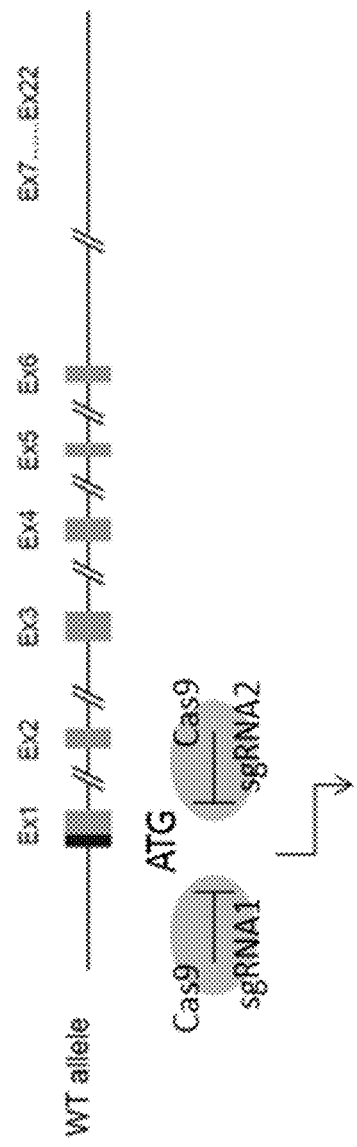
A
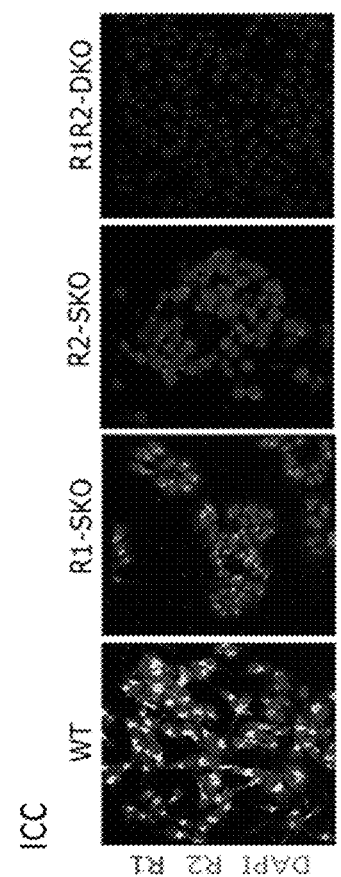
confirmation:
WB
B
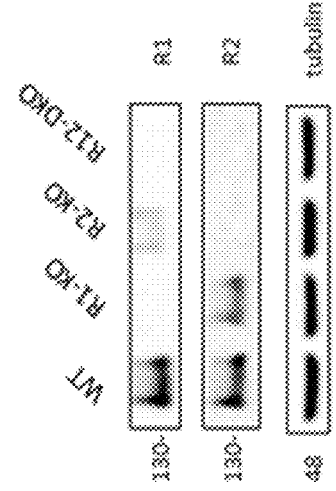
C Figure 15
*in vitro* characterization of IGFR-I 2
A
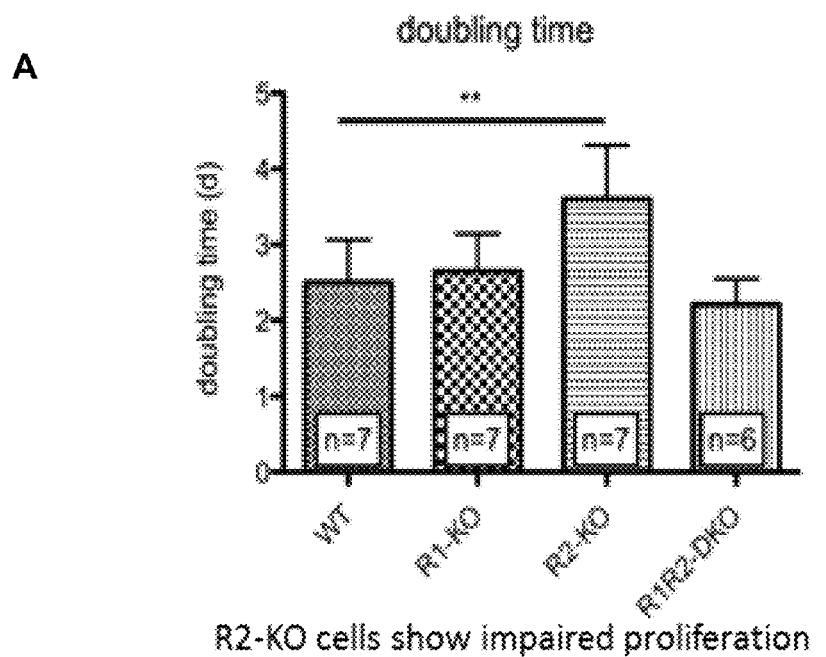
B
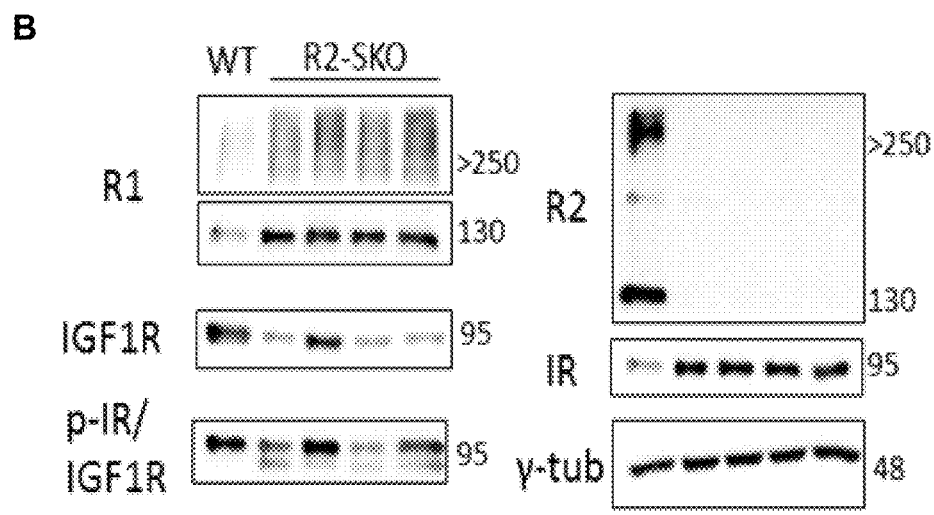

IGFR-I 2 levels are metabolically regulated

IGFR-LIKE 2 RECEPTOR AND USES THEREOF

CROSS REFERENCE TO RELATED APPLICATIONS

This continuation-in-part application claims priority to U.S. application Ser. No. 16/481,781, filed Jul. 29, 2019, which in turn claims priority to International Application No. PCT/EP2018/052267, filed Jan. 30, 2018, which claims the benefit of European Patent Application Serial Number 17153782.2, filed Jan. 30, 2017, and Luxembourg Application Serial Number 100143, filed Mar. 16, 2017, wherein said applications are incorporated herein by reference in their entireties. Also, the entire contents of the ASCII text file entitled "IPM0120US2_Sequence_Listing.txt" created on Aug. 25, 2021, having a size of 26 kilobytes is incorporated herein by reference.

BACKGROUND

The insulin/insulin-like growth factors (IGFs) constitute a network of ligands, cell-surface receptors, and binding proteins involved in the regulation of multiple physiological and pathological processes. Insulin/IGFs play key developmental and metabolic roles at every stage of life. Insulin/IGF signaling also contributes to regulation of lifespan, while dysregulation of signaling has been implicated in neoplasia. Although the insulin receptor (InsR) and IGF-1 receptor (IGF1R) share the majority of their downstream cytoplasmic mediators, most experimental and clinical evidence is consistent with the notion that InsR activation (mainly by insulin) leads primarily to metabolic activities, whereas IGF1R activation (mainly by IGF-1 or IGF-2) leads to proliferative and differentiative events (Sarfstein R and Werner H Endocrinology. 2013 May; 154(5):1672-9; Siddle K J Mol Endocrinol. 2011 Jun. 17; 47(1):R1-10).

InsR and IGF1R belong to a family of transmembrane tyrosine kinase-containing receptors. In their mature form, they present as heterotetramers composed of 2 extracellular α-subunits and 2 transmembrane β-subunits harboring the tyrosine kinase activity. Both IGF- and insulin receptors show a high degree of homology (84% in the tyrosine kinase domain, 45%-65% in the ligand binding domain, and above 50% in overall amino acid sequence). In addition, the receptors display a remarkable similarity in genomic organization (Sarfstein R and Werner H, loc. cit.; Arnalez F and Heiman L. Hematol Oncol Clin North Am. 2012 June; 26(3):527-42).

There are also "hybrid" receptors composed of half an insulin receptor and half an IGF receptor (IRαβ linked to IGF1Rαβ). Hybrids bind IGFs with similar affinity to IGFR, but bind insulin with substantially lower affinity than InsR. It is unclear whether hybrid receptors have a distinct physiological role (Sarfstein R and Werner H, loc. cit.; Arnalez F and Heiman L., loc. cit).

The insulin receptor exists in two splice variant isoforms as a result of alternative splicing of the sequence encoded by exon 11; the 'B' isoform recognizes only insulin, but the 'A' isoform, which is the isoform that is most commonly expressed by tumours, recognizes both insulin and IGF1 and 2. Both isoforms are differentially expressed during development, with InsR-A predominantly ex-pressed in fetal tissues and InsR-B predominately expressed in adult tissues, particularly liver, muscle, and adipocytes. The IGF1R displays an opposite pattern of expression, being absent in liver and present at low levels in adipose tissue and at high levels in brain. In addition, and consistent with its potent anti-apoptotic, pro-survival role, the IGF1R is overexpressed in most tumors and malignant cells (Pollak M Nat Rev Cancer. 2012 Feb. 16; 12(3):159-69, Sarfstein R and Werner H, loc. cit.; Siddle K, loc cit).

IGF1 and IGF2 can be expressed in endocrine, paracrine or autocrine manners, the latter being common in transformed cells. The liver is their main site of production. By contrast, insulin production is confined to pancreatic β-cells. Insulin and the IGFs bind with high affinity to their specific receptor and with lower affinity to the non-cognate receptor, with the exception of IGF2, which also binds InsR-A with high affinity (Pollak M, loc cit.; Siddle K, loc. cit.).

Ligand binding induces conformational changes in the structures of the InsR and IGF1R and activates their intrinsic tyrosine kinase activity. Although insulin and IGFs play distinct physiological roles, they utilize the same signaling pathways. Downstream signaling of the InsR and IGF1R is mostly channeled through the MAPK/Ras-Raf-Erk pathway, the phosphatidylinositol-3-kinase/AKT/mTOR (PI3K/AKT) pathway and the Janus kinase/signal transducer and activator of transcription (JAK/STAT) pathway. Ultimately, activation of IGF1R results in increased cell proliferation and decreased apoptosis, whereas activation of the InsR by insulin-binding promotes the storage and synthesis of lipids, protein, and carbohydrates and inhibits their breakdown and release into the circulation. The first step by which insulin increases energy storage or utilization involves the regulated transport of glucose into the cell, mediated by the facilitative glucose transporter Glut4 (Chang et al. Mol Med. 2004 July-December; 10(7-12): 65-71.). Insulin expression is confined to specialized pancreatic β-cells, and under normal circumstances it is tightly regulated by the level of circulating glucose. Insulin-stimulated glucose uptake by classic insulin-sensitive organs (liver, muscle and adipose tissue) reduces circulating glucose levels. The β-cells are thus glucose 'thermostats', sensing glucose and releasing insulin to maintain physiologic glucose levels within a relatively narrow range. Breakdown of the delicately balanced InsR signaling pathways results in an uncontrolled or impaired insulin-secretion, dysregulated blood glucose levels, and eventually to pancreatic β cell destruction or loss-of-function, a condition commonly known as diabetes (Pollak M, loc cit.; Siddle K, loc. cit.; Sarfstein R and Werner H, loc. cit; Arnalez F and Heiman L., loc. cit)

Diabetes mellitus, affecting 8.3% of the adult population of the world and increasing at an alarming rate, is one of the most common diseases of current era. The number of diabetes mellitus patients is projected to increase from 382 million in 2013 to 592 million by 2035, denoting a net increase of 55%. The predominant form is type 2 diabetes (T2D) which accounts for nearly 90% of all diabetes cases (Hameed et al. World J Diabetes. 2015 May 15; 6(4): 598-612).

Type 1 diabetes (T1D) is an autoimmune disorder afflicting millions of people worldwide and occurs as a consequence of the organ-specific immune destruction of the insulin-producing β-cells in the islets of Langerhans within the pancreas. Once those cells are destroyed, patients with type 1 diabetes lose blood glucose control, which can result in both acute conditions (for example, ketoacidosis and severe hypoglycaemia) and secondary complications (including heart disease, blindness and kidney failure). Type 1 diabetes is thought to develop as a consequence of a combination of genetic predisposition, largely unknown environmental factors, and stochastic events, however, the precise immunologic, genetic and physiologic events that control disease initiation and progression continue to be elucidated.

Early type 2 diabetes (T2D) is caused by insulin resistance of classic insulin-target organs (i.e. reduced uptake of glucose by normal insulin-target cells, often induced by excess calorific intake) leading to hyperinsulinaemia. Initially, these increased levels of insulin are sufficient to overcome insulin resistance and to avoid hyperglycaemia. However, hyperglycaemia eventually occurs not only because of increasing insulin resistance but also because of decreasing insulin output by pancreatic β-cells.

Controlling blood glucose levels is the major goal of diabetes treatment. T1D is commonly managed with administration of insulin as well as dietary changes and exercise. However, the life-long requirement of insulin injections after nutritional intake may severely reduce quality of life of the patient. Moreover, appropriate dosage and timing of insulin injection can prove difficult. Cure or prevention of T1D is severely impaired by the absence of biomarkers that are reliably correlated with the pathogenic process, resulting in β-cell numbers being markedly reduced at the time of diagnosis. The goal of most clinical trials in type 1 diabetes today is to improve functional residual β-cell mass, optimally through induction of immunologic tolerance, while preserving protective immune responses. By definition, this will rarely "cure" the disease because of the significant β-cell destruction that preceded the treatment. Therefore, reliable biomarkers preferably expressed at disease onset would be highly desirable. Other methods focus on the transplantation of either the pancreas or pancreatic β-cells to reconstitute the insulin-secreting function. However, this technique is hampered by a shortage of donor organs. For T2D, besides insulin, other non-insulin therapeutics including synthetic blood sugar lowering agents are available, which are however often limited in terms of their practical effect, convenience of administration, and may elicit adverse reactions.

The safety concerns and adverse effects of available diabetes therapeutics, as well as the lack of permanent remission of disease with any agent tested to date have heightened interest in specific interventions that might modulate the disease.

It is the object of the invention to comply with the needs in the prior art.

SUMMARY

The present inventors observed that the protein encoded by the human KIAA1324L gene, also known as estrogen-induced gene 121 protein (EIG121L) (Uniprot: A8MWY0), strongly co-localizes with the protein encoded by the human KIAA1324 gene, also known as estrogen-induced gene 121 protein (Unmiprot: Q6UXG2), which in turn co-localizes with IGF-1R, IGF-2R and InsR, in particular in the pancreas as described in PCT/EP2016/071126. However, nothing was known, let alone speculated about a role of KIAA1324 or KIAA1324L in metabolism, let alone cancer. This role was for the first time attributed to said proteins by the present inventors.

Due to its domain structure that resembles that of IGFRs, the present inventors assigned to the protein (KIAA1324L/EIG121L) a function of a receptor and thus they called the protein IGFR-like receptor 2 (IGFR-I2; as shown in SEQ ID NO: 2, for example encoded by a nucleotide sequence as shown in SEQ ID NO: 1), while the protein to which IGFR-I2 is co-localized (KIAA1234/Q6UXG2); as described in PCT/EP2016/071126, is referred to herein as IGFR-like receptor 1 (IGFR-I1; as shown in SEQ ID NO. 4, for example encoded by a nucleotide sequence as shown in SEQ ID NO: 3).

In line with a previous invention as described in PCT/EP2016/071126, the present inventors elucidated that either knocking down or knocking-out IGFR-like receptor 1 results in increased phosphorylation of InsR/IGF-1R as well in increased phosphorylation of AMPK, a downstream signaling component that becomes active when either IGFRs or InsR or both transmit a signal, e.g., binding of insulin. Hence, IGFR-like receptor 1 seems to negatively regulate InsR and/or IGF-1R-mediated signaling. Also, with their knowledge of their previous invention, i.e., that the protein encoded by the KIAA1324 gene (IGFR-I1) acts indeed as an IGFR-like receptor, the present inventors, by inspecting genome wide association studies (GWAS), found a strong association of SNPs in the KIAA1324 gene with type 2 diabetes, LDL cholesterol and/or coronary artery disease.

In sum, the protein encoded by the human KIAA1324 gene (IGFR-I1) which the present inventors assigned a function of a modulator of IGF-1R and/or InsR, plays a role in metabolism, in particular in insulin signaling and also likely in LDL cholesterol metabolism as well as in attending ills such as coronary heart disease. This finding was of outstanding importance, since it was not believed that apart from IGFRs and InsR, there may be a further player in insulin signaling. Due to its presumed negative regulatory function on IGFRs and/or InsR (see FIG. 3), the IGFR-like receptor 1 of the previous invention as described in PCT/EP2016/071126 is an attractive target for modulators and may thus open new avenues for the development of medicaments, e.g. for treating diabetes, LDL cholesterol-associated disorder as well as coronary artery disease, particularly however diabetes mellitus type II. Indeed, as shown herein IGFR-like receptor 1 mediates InsR and IGF1R internalization (see FIG. 5). The now identified IGFR-like receptor 2 is assumed to be also involved in InsR and IGF1R internalization due to its interaction with IGFR-like receptor 1.

The inventors of the present invention now found that the protein described herein, IGFR-I2, strongly co-localizes and endogenously interacts with the previously described IGFR-I1 (see FIGS. 1, 2 and 6), presumably by forming IGFR-I1/IGFR-I2-heterodimers. In accordance with the present invention, it was also found that IGFR-I2 exhibits binding motifs that link to RTK signaling pathway and glucose and lipid metabolism. In particular, the present inventors surprisingly observed that decreasing levels of IGFR-I2 lead to increased InsR and IGF1R levels and downstream pathway activation. In this regard it could be observed that reduction of IGFR-like 2 levels leads to modulation of IGFR-like receptor 1 levels, suggesting that IGFR-like 2 regulates internalization, degradation or recycling of IGFR-like 1. Moreover, reduction of IGFR-like 2 levels leads to upregulation of IR and IGF1R (p-IR/IGF1R) and downstream pathway activation (p-Akt), (see FIG. 11). Further, double knock-out of IGFR-like 2 leads to upregulation of IR and IGF1R (p-IR/IGF1R) and downstream pathway activation (p-Akt), (see FIG. 11). Western blot (WB) analysis of Min6 cells grown in 10% FCS and 25 mM glucose revealed that R2-het showed half the levels of R2 and also reduced levels of R1 (compare R1 and R2 WB). Interestingly, knock-out of one allele for IGFR-like 2 leads to decreased levels of IGFR-like 1 and increased levels of Insulin receptor (IR) an IGF1 receptor (IGF1R) levels and activation (p-IR/IGF1R). This in turn leads to increased activation of Akt (p-Akt), a downstream signaling component that becomes active when either IGFRs or InsR or both transmit a signal, e.g., binding of insulin. Double knock-out of IGFR-like 1 and 2 showed a similar increase in IR and IGF1R levels and activation. Thus, knocking down or knocking-out IGFR-like receptor 2 results in increased phosphorylation of InsR and IGF1R as well in increased phosphorylation of Akt. Hence, as already described for IGFR-like receptor 1 in PCT/EP2016/071126, also IGFR-like receptor 2 seems to negatively regulate InsR and/or IGFR-mediated signaling. Accordingly, the protein encoded by the human KIAA1324L gene which the present inventors assigned a function of a modulator of IGFR-like 1 seems to play an important role as modulator of IGF1R and/or InsR, thereby affecting metabolism and insulin signaling. Due to its presumed negative regulatory function on IGFRs and/or InsR, IGFR-like 2 of the present invention appears to be an attractive target for modulators and may thus open new avenues for the development of medicaments.

Accordingly, in context with the present invention, IGFR-I2 appears to be a target for treating medical conditions associated with metabolic disorders such as, e.g., diabetes, particularly type 1 diabetes, type 2 diabetes, gestational diabetes, prediabetes, insulin resistance, metabolic syndrome, and impaired glucose tolerance. Such treatment may be accomplished by antibodies directed against IGFR-I2 or antibodies directed against the interaction surface or positions between IGFR-I1 and IGFR-I2. Also, given the role of EIG 121 (IGFR-I1) in cancer (e.g., endometrial cancer, gastric cancer, breast cancer, prostate cancer, lung cancer, brain cancer (in particular pituitary gland cancer) and others), the co-localization and binding ability of IGFR-I2 to IGFR-I1 identifies IGFR-I2 as target molecule in the treatment of cancer. In context with the present invention, such treatment of cancer may be achieved by antagonists or agonists of IGFR-I2, depending on the role IGFR-I1 plays in different cancer types, i.e. either a cancer activating (proliferation) effect, or a cancer inhibiting effect, respectively.

Also, antagonists or agonists of IGFR-I2 open up new and urgently needed possibilities to revert, e.g. insulin resistance as commonly seen in diabetes mellitus type II pathogenesis or to block insulin signaling. Strikingly, the present inventors could also previously show that the IGFR-like receptor 1 is associated with β cell de-differentiation in the pancreas, an early event in disease onset that ultimately leads to β cell destruction or loss-of-function. Hence, the IGFR-like receptor 2 which strongly co-localizes with IGFR-I1 and seems to negatively regulate InsR and/or IGFR-mediated signaling may also be a promising diagnostic tool enabling early diagnosis and/or treatment of diabetes before irrevocable loss of β cells, thereby potentially paving the way for the treatment of diabetes mellitus type I.

Accordingly, the present invention provides an isolated DNA sequence encoding an IGF receptor (IGFR)-like receptor 2 which is capable of reacting with antibodies raised against an IGFR-like receptor 2 of SEQ ID No: 2 (amino acid sequence IGFR-I2), wherein said antibodies preferably specifically bind to said IGFR-like receptor 2 of SEQ ID NO: 2. In particular, said antibodies specifically bind to the extracellular domain of said IGFR-like receptor 2 of SEQ ID NO: 2. The extracellular domain is assumed to encompass the region between amino acid positions 48 to 929 of SEQ ID NO: 2.

In particular, said isolated DNA sequence may encode an IGFR-like receptor 2 comprising a sequence corresponding to SEQ ID No. 2. The isolated DNA sequence may in particular comprise a sequence corresponding to SEQ ID No. 1 (cDNA IGFR-I2).

Further provided herein is a vector comprising the DNA sequence as described herein. Said vector may further comprise a gene regulation element operatively linked to the DNA sequence encoding said IGFR-like receptor 2 of SEQ ID NO: 2. A host cell comprising said vector is also envisaged.

Further provided herein are binding agents capable of specifically binding an IGFR-like receptor 2, said IGFR-like receptor 2 comprising a sequence corresponding to sequence SEQ ID No. 2 for use as a diagnostic marker for diabetes or the risk of developing diabetes.

Antagonists and agonists of the IGFR-like receptor 2 of the invention, said IGFR-like receptor 2 comprising for example a sequence corresponding to SEQ ID No. 2, are also provided herein. Said antagonists and agonists are in general envisaged for use as a medicament. Specifically, the antagonists and agonists provided herein are intended for use in a method of prophylactic and/or therapeutic treatment of cancer, e.g., endometrial cancer, gastric cancer, breast cancer, prostate cancer, lung cancer, brain cancer (in particular pituitary gland cancer) or of metabolic and endocrine disorders such as, e.g., diabetes. Antagonists are however preferred, particularly for treating metabolic disorders such as diabetes.

The antagonists and agonists are envisaged to bind specifically to said IGFR-like receptor 2 of SEQ ID NO: 2 and may be selected from inter alia an antibody, a siRNA, a nucleic acid, an aptamer, a peptide, a protein, or a small molecule organic compound etc. The antibody may be a monoclonal or polyclonal antibody, for example a monoclonal antibody.

In particular, said antibody, which is preferably a monoclonal antibody, may be an antibody (e.g. a monoclonal antibody) specifically binding to an epitope of said IGFR-like receptor 2, for example said epitope being located within the extracellular domain of IGFR-I2 (SEQ ID NO: 2)

In the diagnostic and/or therapeutic uses provided herein, diabetes is envisaged to comprise type 1 diabetes, type 2 diabetes, gestational diabetes, prediabetes, insulin resistance, metabolic syndrome, and impaired glucose tolerance.

Treatment with the antagonist or agonist of IGFR-like receptor 2 of SEQ ID NO. 2, antagonists being preferred, may prevent or reverse insulin resistance and/or reverse de-differentiation and/or loss-of-function of pancreatic β-cells.

For therapeutic uses to treat cancers as provided herein, antagonists or agonists to IGFR-I2 may be used, e.g., which effect reduction of proliferation and/or induction of apoptosis of cancer cells.

Further provided herein is a medicament or a pharmaceutical composition comprising an antagonist or agonist of IGFR-like receptor 2 (antagonists being preferred). In a preferred embodiment said IGFR-like receptor 2 comprises or consists of a sequence corresponding to SEQ ID No. 2. Said antagonist or agonist is in a preferred embodiment a monoclonal antibody that specifically binds to said IGFR-like receptor 2.

Said preferably monoclonal antibody is in particular envisaged to bind to an epitope of said IGFR-like receptor 2 within its extracellular domain).

Further provided herein is an antibody, preferably a monoclonal antibody which specifically binds to IGFR-like receptor 1 and/or 2, thereby interrupting interaction of IGFR-I1 and IGFR-I2.

Further provided herein is an in vitro screening assay for antagonists or agonists of an IGFR-like receptor 2, said method comprising the steps of:

(a) providing a stable cell line expressing said IGFR-like receptor 2;
(b) contacting said cell line of (i) with a candidate antagonist or agonist; and
(c) measuring or detecting an IGFR-like receptor 2 downstream signaling event, wherein an antagonist is identified by suppressing said IGFR-like receptor 2 downstream signaling event, and an agonist is identified by promoting said IGFR-like receptor 2 downstream signaling event.

Said IGFR-like receptor 2 comprises in a preferred embodiment a sequence corresponding to sequence SEQ ID No. 2.

Also provided herein is an IGFR-like receptor 2 antagonist or agonist obtainable by the in vitro screening assay, said IGFR-like receptor 2 antagonist or agonist being selected from an antibody, a siRNA, a nucleic acid, an aptamer, a peptide, a protein, or a small molecule organic compound.

The present invention also relates to the use of the binding agents of the invention and in particular of the antibodies of the invention for the in vitro detection of degeneration of pancreatic islet cells. The use of these antibodies for the preparation of a therapeutic or diagnostic composition is also contemplated.

Further provided herein is a method of treating diabetes, comprising administering an IGFR-like receptor 2 antagonist or agonist to a subject, said IGFR-like receptor 2 comprising a sequence corresponding to SEQ ID No. 2.

Further provided herein is a method of treating cancer (e.g., endometrial cancer, gastric cancer, breast cancer, prostate cancer, lung cancer, brain cancer (in particular pituitary gland cancer)), comprising administering an IGFR-like receptor 2 antagonist or agonist to a subject, said IGFR-like receptor 2 comprising a sequence corresponding to SEQ ID No. 2.

DESCRIPTION OF THE FIGURES

The invention will be better understood with reference to the detailed description when considered in conjunction with the non-limiting examples and the accompanying drawings. The figures illustrate embodiments of methods of the invention.

Co-immunoprecipitation using antibodies against cytoplasmic domain of IGFR-I 1 (36D7) can efficiently pull down IGFR-I 2 in Min6 wild-type cells (WT), but not in IGFR-I 1 knock-out cells (right upper side).

Co-immunoprecipitation using antibodies against cytoplasmic domain of IGFR-I 2 (28A5) only inefficiently pulls down IGFR-I 1 in Min6 wild-type cells (WT), but not in IGFR-I 1 knock-out cells (left lower side). Interaction of IGFR-I1 and IGFR-I2 is interrupted.

Co-immunoprecipitation using antibodies against cytoplasmic domain of IGFR-I 2 (28G11) can efficiently pull down IGFR-I 1 in Min6 wild-type cells (WT), but not in IGFR-I 1 knock-out cells (right lower side).

Conclusion: Homo- and/or heterodimerization of IGFR-I1 and 2 can be blocked using an antibody approach, similar to the strategy used for ErbB2 and the Herceptin antibody which blocks dimerization of the ErbB2 monomer.

Figure 3:
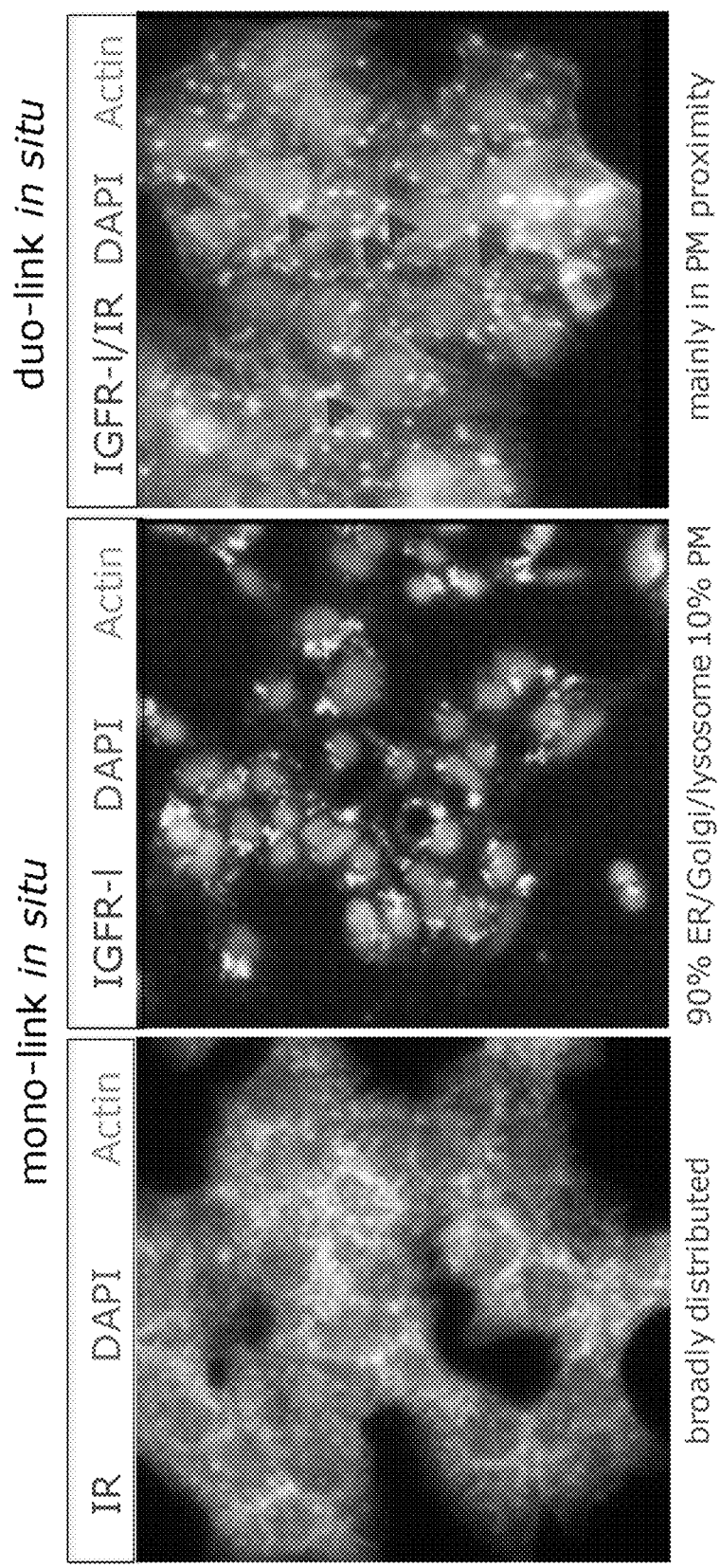

FIG. 3: Duo-link in situ fluorescence reveals IR-IGFR-I1 interaction close to plasma membrane.

Figure 4:
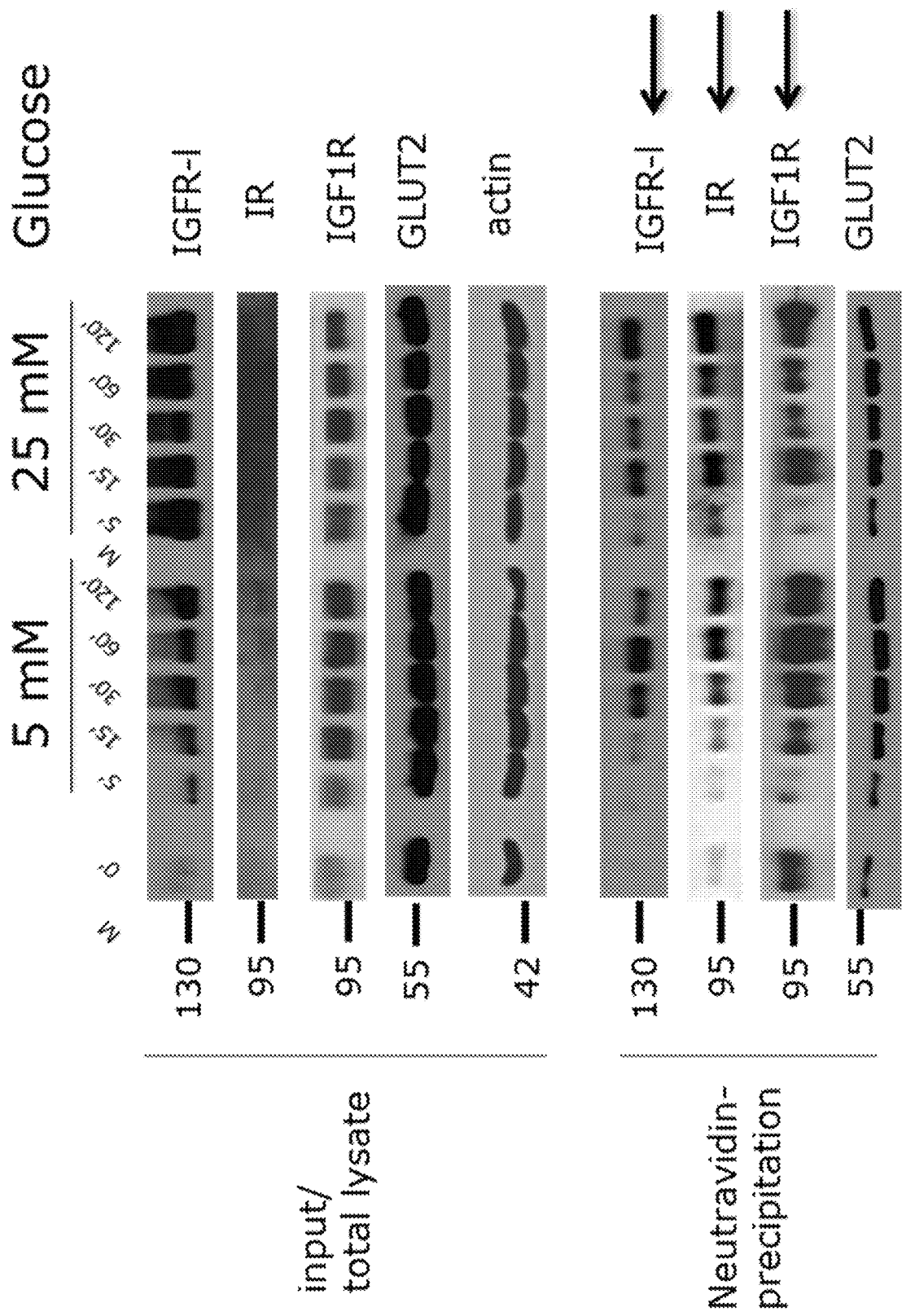

FIG. 4: IGFR-I1, IR and IGF1R show identical translocation kinetics to PM after glucose induction. Surface biotinylation assay shows that after serum and glucose starvation for 2 h, IGFR-I1, IR and IGF1R quickly translocate to the plasma membrane with peak levels after 30, 60 and 120 min. These results show that these receptors in glucose-dependent manner get transported to the plasma membrane, as it is also well known for the glucose transporter GLUT2. Assays were done in mouse Min6 insulinoma cell lines.

Figure 5:
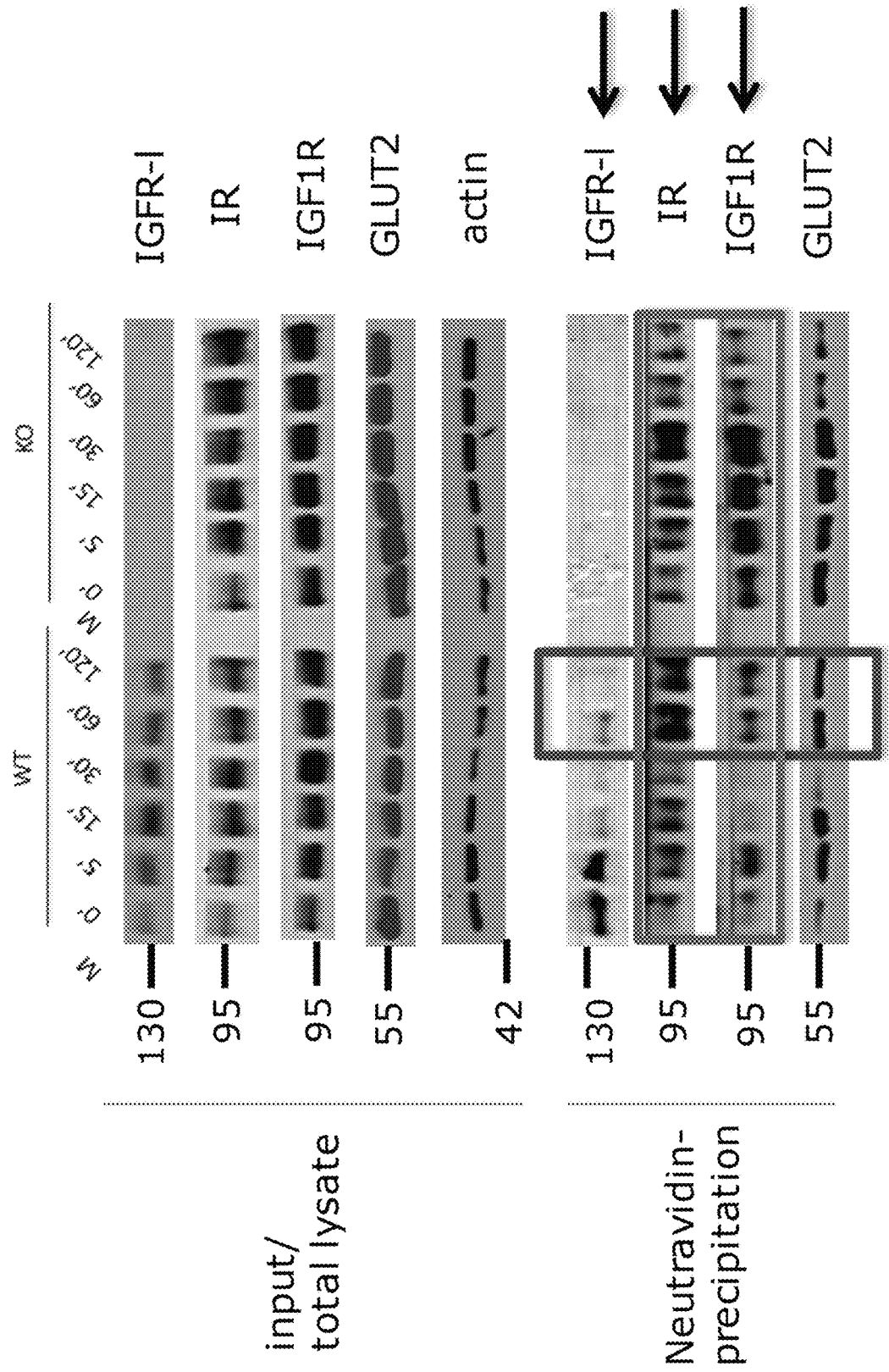

FIG. 5: IGFR-I1 mediates IR and IGF1R internalization. Surface biotinylation assay shows that after glucose and serum exposure (0 min) starvation for 2 h leads to rapid internalization of IGFR-I1, IR and IGF1R after 5-15 min and re-cycling of IR and IGF1R after 60-120 min in mouse Min6 insulinoma cell lines (WT, left side). Knock-out of IGFR-I1 shows that internalization of IR and IGF1R and GLUT2 is impaired, as shown by the prolonged plasma membrane (PM) retention (KO, right side). HBSS is glucose and serum free, so without growth factors. This shows that IGFR-I1 is necessary for the internalization of IGF1R and IR.

Figure 6:

FIG. 6: IGFR-I2 is a high affinity endogenous interaction partner. Co-immunoprecipitation using antibodies against IGFR-I 1 can efficiently pull down IGFR-I 2 in Min6 wild-type cells (WT), but not in IGFR-I 1 knock-out cells (left side). Co-immunoprecipitation using antibodies against IGFR-I 2 can efficiently pull down IGFR-I 1 in Min6 wild-type cells (WT), but not in IGFR-I 1 knock-out cells (right side). These results show that IGFR-like 1 and 2 physically interact on endogenous level in Min6 insulinoma cells.

FIG. 7: cDNA sequence encoding IGFR-I2 (SEQ ID NO: 1).

FIG. 8: IGFR-I2 amino acid sequence (SEQ ID NO: 2).

FIG. 9: cDNA sequence encoding IGFR-I1 (SEQ ID NO: 3).

FIG. 10: IGFR-I1 amino acid sequence (SEQ ID NO: 4).

Figure 11:
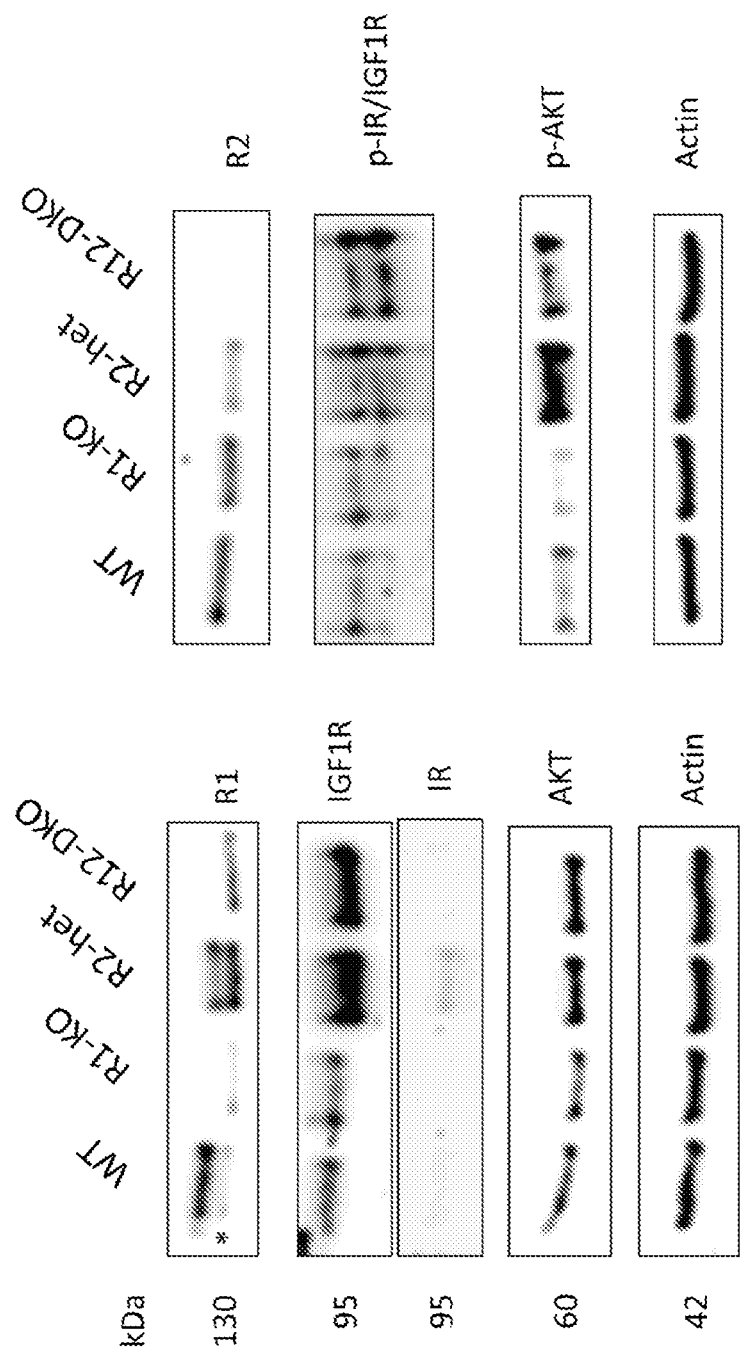

FIG. 11: IGFR-like receptor knockdown and knockout in Min6 cells. Western blotting analysis of phosphorylated Insulin receptor (IR), phosphorylated IGF1 receptor and downstream signaling molecule Akt, which is an important molecule commonly phosphorylated as a consequence of IR or IGFRs or both activation. CRISPR/Cas9-mediated gene knock-out in Min6 insulinoma cells (grown in 10% FCS and 25 mM glucose) resulted in full knock-out of IGFR-like 1 (R1), heterozygous deletion of IGFR-like 2 (R2-het) and double homozygous knock-out of IGFR-like 1 and 2 (R12-DKO). Lower band as indicated by an asterisks (*) in R1 WB is an unspecific band due to cross-reactivity. R2 knock-out in R12-DKO is not complete, but rather 80-90%. Reduction of IGFR-like 2 levels (R2-het) leads to upregulation of IR and IGF1R (p-IR/IGF1R) and downstream pathway activation (p-Akt). Double knock-out of IGFR-like 1 and 2 leads to upregulation of IR and IGF1R (p-IR/IGF1R) and downstream pathway activation (p-Akt). Reduction of IGFR-like 2 levels leads to modulation of IGFR-like receptor 1 levels, suggesting that IGFR-like 2 regulates internalization, degradation or recycling of IGFR-like 1.

FIG. 12: (A) IGFR-I 2 (R2) expression in vivo is shown by immunohistochemistry of pancreas and pituitary tissue sections as well as by Western blot (WB) of isolated islets. In the Islets of Langerhans, IGFR-I 2 can be detected in insulin-producing β-cells (see magnification). In the pituitary, IGFR-I 2 expression seems to be restricted to subtypes of hormone-producing cells. This might implicate an important role of IGFR-I 2 in the regulation of the hypothalamic-pituitary-gonadal (HPG) axis which controls growth and metabolism.

(B) We also found IGFR-I 2 expressed in the human β-cell line EndoC, where it shows distinct subcellular localization when compared to its paralog IGFR-I 1, suggesting a specific role for both proteins. Initially, IGFR-I 1 (R1) was described as estrogen-induced gene being regulated in endometrial cancer. We additionally detected IGFR-I 2 in the estrogen-dependent human breast cancer cell line MCF7.

Figure 13:
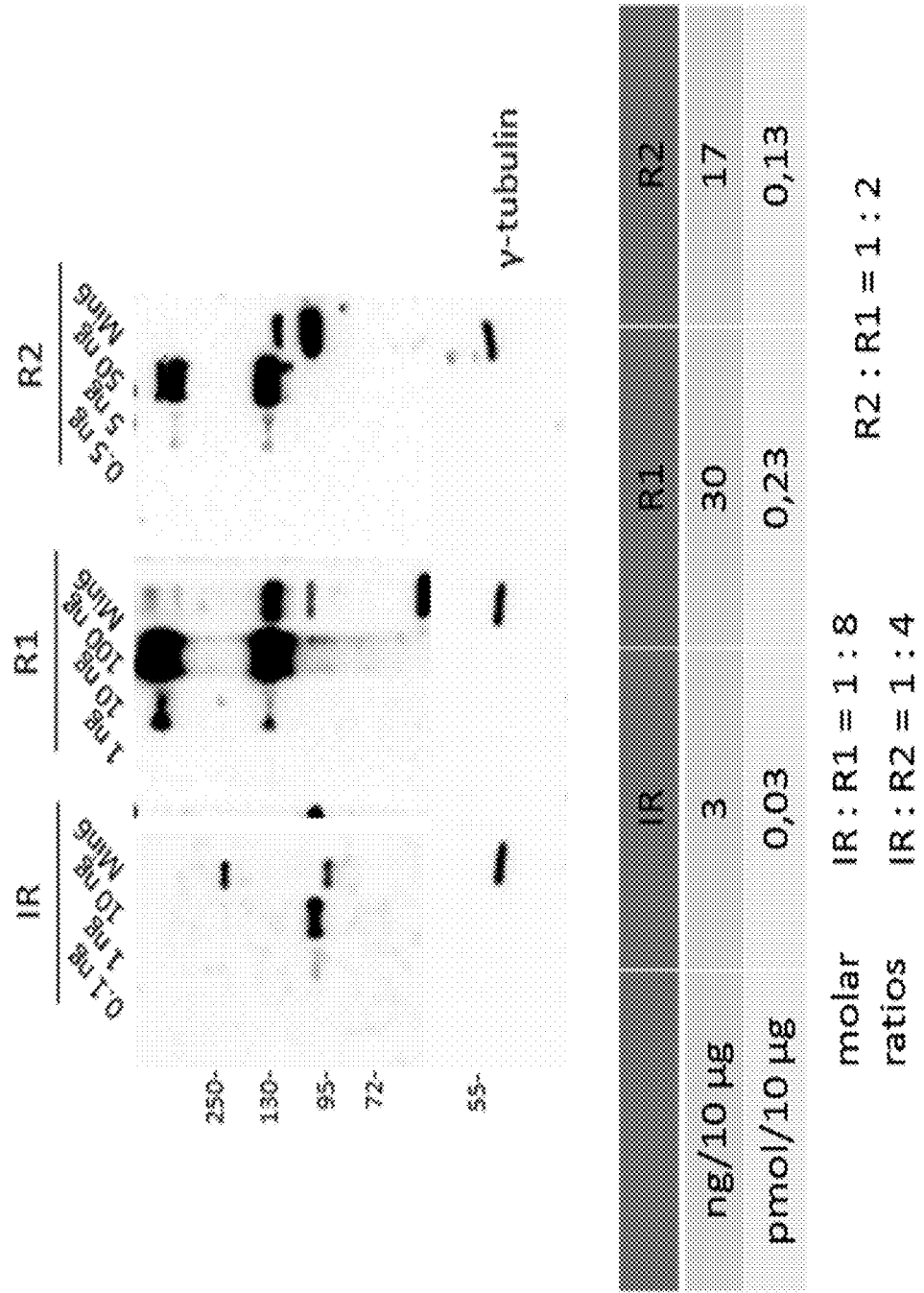

FIG. 13: Absolute expression of Insulin receptor (IR), IGFR-I 1 (R1) and IGFR-I 2 (R2) in mouse Min6 insulinoma cell line was analyzed by acquiring a standard curve from three defined concentrations of purified full-length receptors. This shows a very high expression of both receptors in pancreatic β-cells.

FIG. 14: (A) A CRISPR/Cas9-mediated single knock-out (SKO) and double KO of IGFR-I 1 (R1) and 2 (R2) were generated by targeting the start codons (ATG) with two different pairs of sgRNAs. The lack of protein expression was confirmed in Western Blot (B) and immunocytochemistry (C).

Figure 15:
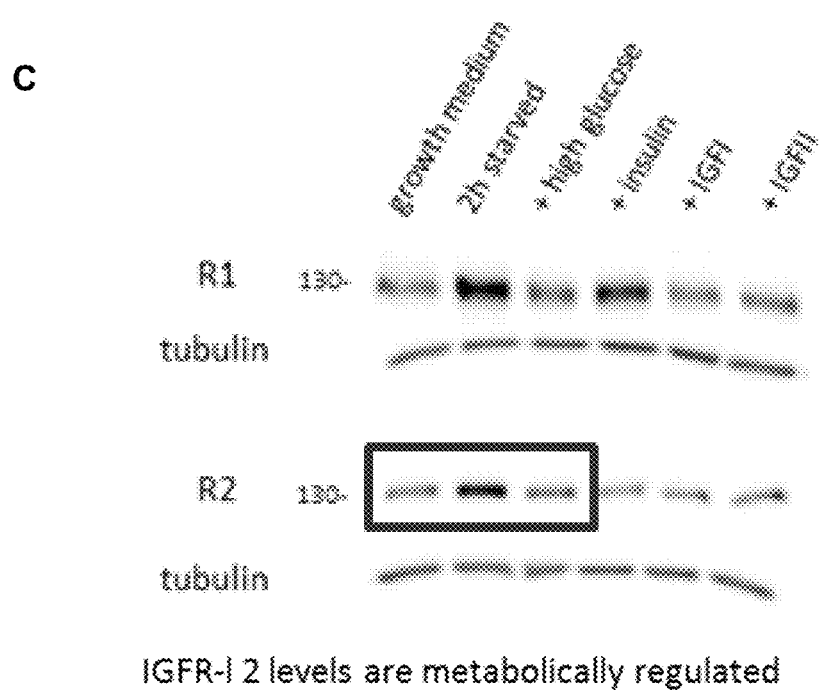

FIG. 15: (A) Analysis of the IGFR-I 2 (R2) KO cells revealed an impaired proliferation when compared to WT, IGFR-I 1 (R1) KO and IGFR-I 1 and 2 (R1R2), which is demonstrated by a slower doubling time. (B) This correlated with decreased levels of IGF1R and activated p-IR/IGF1R necessary for cell proliferation and survival. Increase of Insulin receptor (IR) might hint to a higher metabolic activity. (C) Moreover, IGFR-I 2 protein is regulated metabolically during starvation showing increased levels protein at 2 h of nutrient deprivation. Overall, the data suggest that IGFR-I 2 is a functional modulator of the Insulin receptor IGF1R signaling system and might have a role in regulating cellular metabolism and/or proliferation.

DETAILED DESCRIPTION

The present inventors have surprisingly discovered a novel IGFR-like receptor 2 (IGFR-I2) which is strongly co-localized to and endogenously interacts with a previously described IGFR-like receptor 1 (IGFR-I1; KIAA1234; EIG122), the latter is expressed adjacent to IGF-1, IGF-2 and Insulin ligands in the pancreas, and demonstrated to negatively regulating InsR and/or IGF1R-mediated signaling. In this regard the present inventors surprisingly figured out that downregulation or knockout of IGFR-like receptor 2 leads to modulation (up- and downregulation) of IGFR-like receptor 1 levels, suggesting that IGFR-like 2 regulates internalization, degradation or recycling of IGFR-like 1. Additionally, knocking down or knocking-out IGFR-like receptor 2 leads to upregulation of IR and IGF1R by phosphorylation of InsR and IGF1R, as well as to increased phosphorylation of Akt, a downstream signaling component that becomes active when either IGFRs or InsR or both transmit a signal, e.g. binding of insulin. Hence, as already described for IGFR-like receptor 1 in PCT/EP2016/071126, also IGFR-like receptor 2 seems to negatively regulate InsR and/or IGFR-mediated signaling, thereby affecting metabolism and/or growth (proliferation). Therefore, antagonists and agonists of IGFR-I2 open up new and urgently needed possibilities to revert insulin resistance as commonly seen in diabetes pathogenesis or to block insulin signaling. Also, the present inventors could previously also show that the IGFR-like receptor 1 is associated with β cell de-differentiation in the pancreas, an early event in disease onset that ultimately leads to β cell destruction or loss-of-function. Hence, the IGFR-like receptor 2 as described in context with the present invention may also be a promising diagnostic tool enabling early diagnosis and treatment of diabetes before irrevocable loss of β cells.

The present inventors previously pioneered in elucidating the function of the human KIAA1324 gene in encoding an IGFR-like receptor 1 as described herein. The protein product of KIAA1324 previously referred to as UPF0577 protein KIAA1324 or Estrogen-induced gene 121 (EIG121) protein has commonly been known as a cancer marker and further identified the pivotal role of IGFR-I1 in metabolism to the protein. Thus, the newly identified interaction partner of IGFR-I1 as described herein, namely IGFR-I2, also appears to play a decisive role in conditions associated with IGFR-I1, i.e. cancer as well as metabolism as described herein.

In a first aspect, the invention thus provides an isolated DNA sequence encoding an IGF receptor (IGFR)-like receptor 2 which is capable of reacting with antibodies raised against an IGFR-like receptor 2 of SEQ ID No: 2, wherein said antibodies specifically bind to said IGFR-like receptor 2 of SEQ ID NO. 2

In particular, said isolated DNA sequence is envisaged to encode protein KIAA1324L with Uniprot Acc. No. A8MWY0, the amino acid sequence as shown in SEQ ID No.: 2 or a functional variant thereof, said proteins also referred to as "IGFR-like receptor 2" or "IGFR-I2" herein.

Importantly, expression of the "EIG121" gene (IGFR-I1) which strongly co-localizes or interacts with/binds to IGFR-I2 as shown in context with the present invention was known for its role in neoplastic proliferations (particularly cancer) associated with estrogen excess and was previously also identified to be a target for antagonists or agonists to treat metabolic disorders such as diabetes.

Functional variants of the IGFR-like receptor 2 disclosed herein, which have a threshold sequence identity or sequence homology to the IGFR-like receptor described herein, are also encompassed by the term "IGFR-like receptor 2" or "IGFR-I2". Said functional variants are envisaged to have at least 50%, 55%, 60%, 65%, 70%, 75%, 80%, 85%, 90%, 95%, 97%, 98%, 99%, 99.5% or 100% sequence identity with SEQ ID No.: 2 and are capable of reacting with antibodies raised against an IGFR-like receptor 2 of SEQ ID No: 2, wherein said antibodies specifically bind to said IGFR-I2, preferably to an epitope within the extracellular domain thereof.

It is further envisioned that said functional variants preferably exhibit the same properties as IGFR-I2, i.e. interact or bind to IGFR-I1 as shown herein and in the examples and inhibit or reduce InsR and/or IGF1R-mediated signaling, in particular Akt phosphorylation and/or phosphorylation of other downstream signaling components that become active when either IGFRs or InsR or both transmit a signal. The term "% identity" or "% sequence identity" as used herein refers to the percentage of pair-wise identical residues—following (homologous) alignment of a sequence of a polypeptide of the invention with a sequence in question—with respect to the number of residues in the longer of these two sequences. Percent identity is determined by dividing the number of identical residues by the total number of residues and multiplying the product by 100. The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of two proteins. Preferably, the amino acid sequence shown in SEQ ID NO:2 is preferred as a "reference sequence". The term "reference sequence" and "wild type sequence" (of the IGFR-like receptor 1 or 2) is used interchangeably herein.

Figure 1:
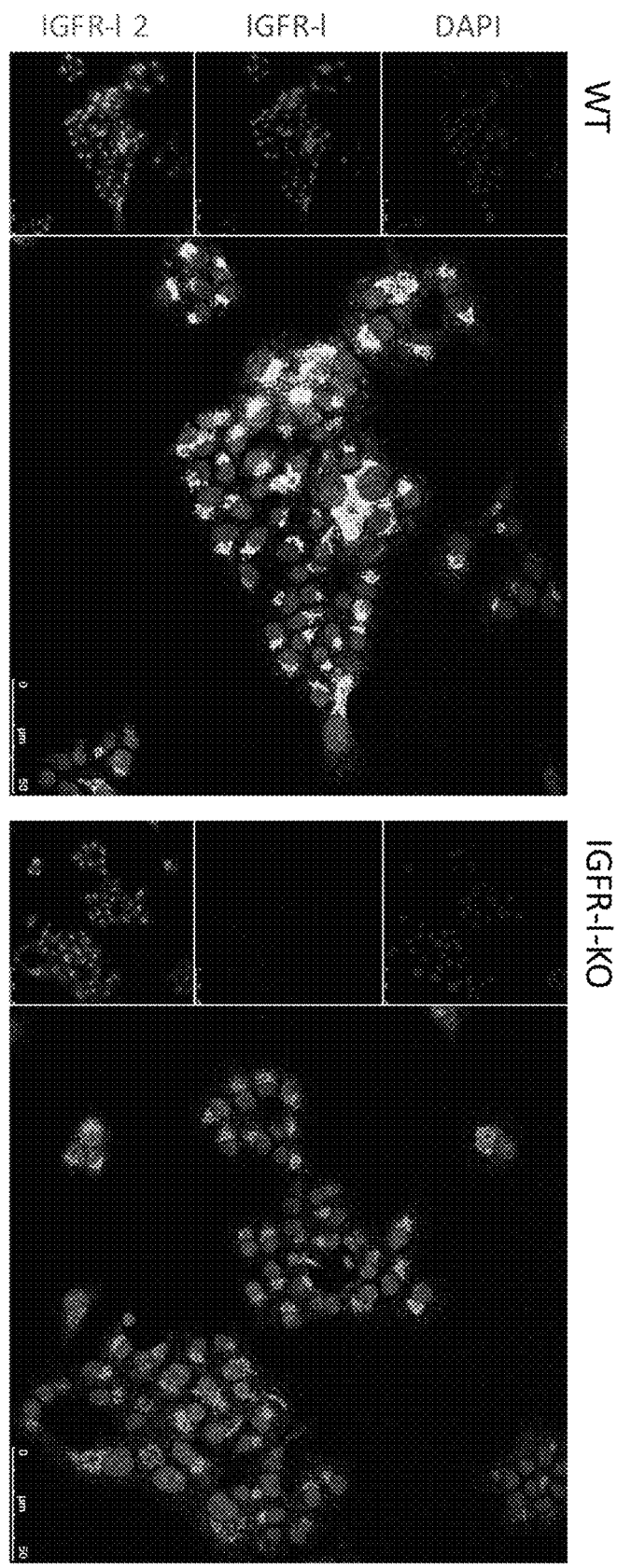
FIG. 1: Co-localization of IGFR-I 2 and IGFR-I 1 in Min6. Co-immunostaining experiments using antibodies against IGFR-I 1 (red) and IGFR-I 2 (green) show perfect co-localization of both proteins in endoplasmic reticulum, Golgi, lysosome and plasma membrane in Min6 wild-type cells (left side), but not in IGFR-I 1 knock-out cells (right side).
Figure 2:
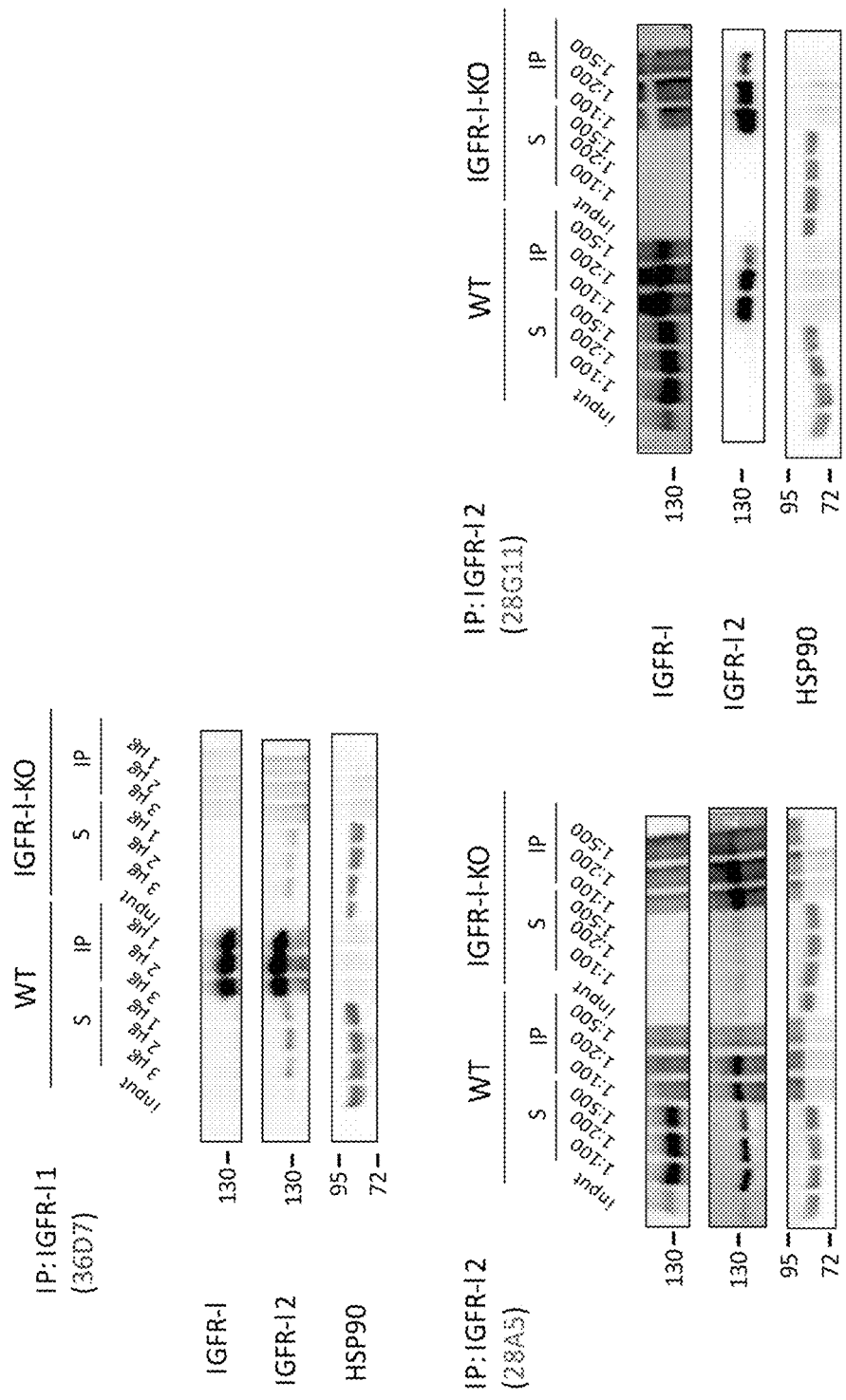
FIG. 2: Interaction of IGFR-I and IGFR-I2 is interrupted by antibody binding.

As used herein, the term "binding" or "interacting" in context with binding or interaction between IGFR-I2 and IGFR-I2 means strong co-localization as shown and described herein, or may also refer to the formation of dimers (dimerization), e.g., the formation of heterodimers of IGFR-I2 and IGFR-I1. In context with the present invention, such binding can be shown, e.g., by applying co-immunoprecipitation assays as shown and described herein, where (monoclonal) antibodies are directed to IGFR-I1, thereby also allowing "pulling down" or staining of IGFR-I2 (see, e.g., FIG. 2, upper right) where for example mAb 36D7 may be used, or vice versa (see, e.g., FIG. 2, lower right), where for example mAb 28G11 may be used. Other suitable methods to identify binding/interaction or other strong co-localization between IGFR-I1 and IGFR-I2 are further described herein, e.g., as shown in FIGS. 1 and 6.

The percentage of sequence homology or sequence identity can, for example, be determined herein using the BLASTP, version blastp 2.2.5 (Nov. 16, 2002; cf. Altschul, S. F. et al. (1997) Nucl. Acids Res. 25, 3389-3402). In this embodiment the percentage of homology is based on the alignment of the entire polypeptide sequences (matrix: BLOSUM 62; gap costs: 11.1) including the propeptide sequences, preferably using the wild type protein scaffold as reference in a pairwise comparison. It is calculated as the percentage of numbers of "positives" (homologous amino acids) indicated as result in the BLASTP program output divided by the total number of amino acids selected by the program for the alignment.

In the context of the invention, the expression "position corresponding to another position" (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid position corresponding to amino acid position [X]" of a specified protein sequence represents, in addition to referral to amino acid positions of the specified protein sequence, referral to a collection of equivalent positions in other recognized protein and structural homologues and families. The same may be applied to the expression "sequence corresponding to sequence", mutatis mutandis. I.e., the referral to a sequence "corresponding to" a specified protein sequence [X], in addition to referral to sequence the specified protein sequence, referral to a collection of equivalent sequences in other recognized protein and structural homologues and families.

The term "InsR" or "IR" refers to the insulin receptor and generally comprises both the IR-A (also known as "isoform short") and IR-B (also known as "isoform long") isoforms. The InsR occurs as a tetramer of 2 α chains carrying the insulin-binding regions and 2 β chains carrying the kinase domain, linked by disulfide bonds. The InsR is a receptor tyrosine kinase that is activated by binding of insulin, IGF-1 and IGF-2, ultimately leading to signaling through the MAPK/Ras-Raf-Erk pathway, the phosphatidylinositol-3-kinase/AKT/mTOR (PI3K/AKT) pathway and/or the Janus kinase/signal transducer and activator of transcription (JAK/STAT) pathway. More precisely, ligand binding to the α-chains of the InsR ectodomain induces structural changes within the receptor leading to autophosphorylation of various tyrosine residues within the intracellular tyrosine kinase domain of the β-chain, leading to recruitment and phosphorylation of several intracellular substrates, including, insulin receptor substrates (IRS1, 2, 3, 4), SHC, GAB1, CBL and other signaling intermediates. Each of these phosphorylated proteins serve as docking proteins for other signaling proteins that contain Src-homology-2 domains (SH2 domain), including the p85 regulatory subunit of PI3K and SHP2. Phosphorylation of IRSs proteins leads to the activation of two main signaling pathways: the PI3K-AKT/PKB pathway, which is responsible for most of the metabolic actions of insulin, and the Ras-MAPK pathway, which regulates expression of some genes and cooperates with the PI3K pathway to control cell growth and differentiation. Binding of PI3K to phosphotyrosines on IRS1 leads and subsequent PI3K activation leads to the phosphorylation and activation of AKT, AMPK and mTOR, a signaling pathway which regulates metabolism and integrates signals from insulin. InsR activation upon ligand binding also triggers the Ras/RAF/MAP2K/MAPK pathway via phosphorylation of IRS1 and recruitment of GRB2/SOS, which is mainly involved in mediating cell growth, survival and cellular differentiation of insulin.

An illustrative example of the InsR is the human InsR with Uniprot Acc. No. P06213 (entry version 216 of Jul. 22, 2015) and variants thereof. Insulin receptors in the context of the present invention are preferably capable of inducing (i) Akt phosphorylation, and/or (ii) AMPK phosphorylation and/or (iii) mTOR phosphorylation upon binding of their ligand, in particular insulin.

The term "IGF-receptor 1" or "IGF1R" or "IGFRI" is used herein to refer to the Insulin-like growth factor 1 receptor tyrosine kinase. IGF1R binds to IGF1 with high affinity and IGF2 and insulin (INS) with a lower affinity. Ligand binding activates the receptor kinase, leading to receptor autophosphorylation, and phosphorylation of multiple substrates, including, the insulin-receptor substrates (IRS1/2), Shc and 14-3-3 proteins, which ultimately leads to the activation of three main signaling pathways: the PI3K-AKT/PKB pathway, the Ras-MAPK pathway, and the JAK/STAT pathway. The activated IGF1R is involved in cell growth and survival control. Thus, although InsR and IGF1R feed into similar signaling pathways, InsR-mediated signaling predominantly regulates metabolism, whereas IGF1R signaling is involved in cell growth and survival.

An illustrative example of the IGF1R is the human IGF1R with Uniprot Acc. No. P08069 (entry version 185 of Jul. 22, 2015) and variants thereof. IGF1R in the context of the present invention is preferably capable of inducing (i) Akt phosphorylation, and/or (ii) AMPK phosphorylation and/or (iii) mTOR phosphorylation upon binding of their ligand, in particular IGF1.

The term "IGF1" or "IGFI" refers to the Insulin-like growth factor I, a protein structurally and functionally related to insulin, but having a higher growth-promoting activity. An illustrative example is the human IGF1 with Uniprot Acc. No. P05019 (entry version 186 of Jul. 22, 2015). "IGF1" in the context of the present invention is preferably capable of binding to the IGF1 receptor and eliciting IGF1R signaling as described elsewhere herein.

The term "IGF2R" or "IGF2R" or "IGFRII" is used herein to refer to the Insulin-like growth factor 2/mannose-6-phosphate (IGF-2/M6P) receptor. The IGF2R is a single transmembrane protein composed of a large extracytoplasmic (i.e. extracellular) domain, a single transmembrane region and a short cytoplasmic tail that lacks intrinsic catalytic activity. The receptor binds IGF-2 with higher affinity than IGF-1 and does not bind insulin. The IGF2R has been reported to interact, via distinct sites, with lysosomal enzymes and a variety of other M6P-containing ligands, and regulate extracellular IGF-2 concentrations, thereby modulating signaling through the growth-stimulatory IGF-1 receptor pathway.

An illustrative example of the IGF2R is the human IGF2R with Uniprot Acc. No. P11717 (entry version 174 of Jul. 22, 2015) and variants thereof.

The term "IGF2" or "IGFII" refers to the Insulin-like growth factor II. An illustrative example is the human IGF2 with Uniprot Acc. No. P01344 (entry version 199 of Jul. 22, 2015) and variants thereof. "IGF2" in the context of the present invention is preferably capable of binding to the 1G2 receptor.

The isolated DNA sequence provided herein may comprise a sequence corresponding to the sequence of IGFR-I2 as shown in SEQ ID No.: 1, or variants thereof as described herein. Variants of the IGFR-I2 gene may also include orthologs. An ortholog, or orthologous gene, is a gene with a sequence that has a portion with similarity to a portion of the sequence of a known gene, but found in a different species than the known gene. An ortholog and the known gene originated by vertical descent from a single gene of a common ancestor.

As used herein a variant or ortholog of the IGFR-I2 gene is envisaged to encode an IGFR-like receptor 2 or a functional variant thereof, i.e. preferably being capable of interacting or binding to IGFR-I1 and having at least about 60%, 65%, 70%, 75%, 80%, 90%, 95%, 97%, 98%, 99%, 99.5% or 100% sequence identity with the IGFR-I2 gene, i.e. sequence identity with the IGFR-I2 gene's coding sequence shown in SEQ ID NO: 1 (cDNA).

As used herein the term "isolated DNA sequence" refers to a DNA molecule purified, or substantially purified, from endogenous material, including other nucleic acid sequences, proteins, peptides, lipids and so on naturally occurring in the cell and/or organism from which the DNA sequence is derived and includes DNA purified by standard purification techniques as well as DNA prepared by recombinant technology and those chemically synthesized.

Vector

The nucleic acid of the invention may also be in the form of, may be present in and/or may be part of a vector.

The term "vector" refers a nucleic acid molecule used as a vehicle to transfer (foreign) genetic material into a host cell and encompasses—without limitation—plasmids, viruses, cosmids and artificial chromosomes such as bacterial artificial chromosomes (BACs) and yeast artificial chromosomes (YACs). In general, engineered vectors comprise an origin of replication, a multicloning site and a selectable marker. The vector itself is generally a nucleotide sequence, commonly a DNA sequence that comprises an insert (transgene) and a larger sequence that serves as the "backbone" of the vector. Vectors may encompass additional elements besides the transgene insert and a backbone including gene regulation elements, genetic markers, antibiotic resistances, reporter genes, targeting sequences, or protein purification tags. Particularly envisaged within the context of the invention are expression vectors (expression constructs) for expression of the transgene in the host cell, which generally comprise—in addition to the transgene—gene regulation sequences.

An expression vector is, in general, a vector that can provide for expression of the IGFR-like receptor 2 in vitro and/or in vivo (i.e. in a suitable host cell, host organism and/or expression system). The person skilled in the art will readily understand that choice of a particular vector include depends, e.g., on the host cell, the intended number of copies of the vector, whether transient or stable expression of the IGFR-like receptor 2 is envisaged, and so on.

"Transient expression" results from the introduction of a nucleic acid (e.g. a linear or non-linear DNA or RNA molecule) or vector that is incapable of autonomous replication into a recipient host cell. Expression of the transgene occurs through the transient expression of the introduced sequence.

However, "stable expression" of the nucleic acid sequence as described herein will often be preferred and may be accomplished by either stably integrating the nucleic acid sequence into the host cell's genome or by introducing a vector comprising the nucleic acid sequence of the invention and being capable of autonomously replicating into the host cell.

The vector provided herein is in particular envisaged to comprise a gene regulation element operably linked to the DNA sequence encoding said IGFR-like receptor 2.

The term "gene regulation element" refers to DNA sequences necessary for the expression of an operably linked coding sequence in a particular host organism. The term "gene regulation element" includes controllable transcriptional promoters, operators, enhancers, silencers, transcriptional terminators, 5' and 3' untranslated regions which interact with host cellular proteins to carry out transcription and translation and other elements that may control gene expression including initiation and termination codons. The precise nature of the regulatory regions needed for gene expression may vary from organism to organism. Prokaryotic gene regulation elements, for example, include a promoter, optionally an operator sequence, and a ribosome binding site (RBS), whereas gene regulation elements for eukaryotic cells comprise promoters, polyadenylation (poly-A) signals, and enhancers.

The gene regulation element is envisaged to be "operably linked" to the gene to be expressed, i.e. placed in functional relationship with the same. For instance, a promoter or enhancer is "operably linked" to a coding nucleic acid sequence if it affects the transcription of the sequence. The DNA sequences being "operably linked" may or may not be contiguous. Linking is typically accomplished by ligation at convenient restriction sites or synthetic oligonucleotide adaptors or linkers.

Host Cell

Further provided herein is a host cell comprising the vector as described herein.

A variety of host cells can be employed for expressing the nucleic acid sequence encoding the IGFR-like receptor 2 as described herein. Host cells can be prepared using genetic engineering methods known in the art. The process of introducing the vector into a recipient host cell is also termed "transformation" or "transfection" hereinafter. The terms are used interchangeably herein.

Host cell transformation typically involves opening transient pores or "holes" in the cell wall and/or cell membrane to allow the uptake of material. Illustrative examples of transformation protocols involve the use of calcium phosphate, electroporation, cell squeezing, dendrimers, liposomes, cationic polymers such as DEAE-dextran or polyethylenimine, sonoporation, optical transfection, impalefection, nanoparticles (gene gun), magnetofection, particle bombardement, alkali cations (cesium, lithium), enzymatic digestion, agitation with glass beads, viral vectors, or others. The choice of method is generally dependent on the type of cell being transformed, the vector to be introduced into the cell and the conditions under which the transformation is taking place.

As used herein, the term "host cell" refers to any cell or cell culture acting as recipients for the vector or isolated nucleic acid sequence encoding the IGFR-like receptor 2 as described herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

E.g., the IGFR-like receptor 2 can be produced in bacteria. In addition to prokaryotes, eukaryotic microbes such as filamentous fungi or yeast are suitable cloning or expression hosts for the IGFR-like receptor 2 of the invention. Illustrative examples include *Saccharomyces cerevisiae, Schizosaccharomyces pombe, Kluyveromyces* hosts such as *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus; yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger*.

Suitable host cells for the expression of glycosylated antibody construct of the invention may also be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV.

Plant cell cultures of cotton, corn, potato, soybean, petunia, tomato, *Arabidopsis* and tobacco can also be used as hosts. Cloning and expression vectors useful in the production of proteins in plant cell culture are known to those of skill in the art.

Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/-DHFR (CHO), mouse sertoli cells (TM4); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells; MRC 5 cells; FS4 cells; and human hepatoma cells (Hep G2).

Ligands

For IGFR-like receptor 1 as previously described, there were binding sites for potential ligands identified that may inter alia serve as a template for providing the diagnostic binding agents and antagonists or agonists of the present invention. Said domains include two insulin-like growth factor binding domains (domain 1: amino acids 273-413 of SEQ ID NO: 4; domain 2: amino acids 579-659 of SEQ ID No. 4), a mannose-6-phosphate receptor binding domain (M6P domain, amino acids 655-857 of SEQ ID No. 4), a transmembrane domain (amino acids 908-930 of SEQ ID NO: 4) and a cytoplasmic domain (amino acids 932-1013 of SEQ ID No: 4). The present invention thus also relates to binding agents, such as e.g. antibodies (monoclonal antibodies being preferred), that specifically bind to at least one of such above mentioned domains as analogously comprised by IGFR-I2.

Accordingly, for IGFR-like receptor 2 binding sites for potential ligands identified include two insulin-like growth factor binding domains (domain 1: amino acids 283-454 of SEQ ID NO: 2; domain 2: amino acids 600-675 of SEQ ID No. 2), a mannose-6-phosphate receptor binding domain (M6P domain, amino acids 669-876 of SEQ ID No. 2), a transmembrane domain (amino acids 930-950 of SEQ ID NO: 2) and a cytoplasmic domain (amino acids 951-1029 of SEQ ID No: 2).

Proteins comprising an insulin-like growth factor binding domain (InterPro Acc. No. IPR009030) include, without limitation, the insulin-like growth factor-binding proteins (IGFBP1-6), the type-1 insulin-like growth-factor receptor (IGF-1R), the receptor protein-tyrosine kinase Erbb-2, Erbb-3 and Erbb-4 (ErbB2, -3, -4), Ephrin Type A/B receptor, epidermal growth factor receptor (EGFR), EGFR-like binding proteins, CYR61, Matrilin-2, -3 and -4, Delta-like protein 1, Cubilin, Slit homolog 1 and 3 protein, Multiple epidermal growth factor-like domains protein 6, Low-density lipoprotein receptor-related protein 4, WNT1-inducible-signaling pathway protein 2, WNT1-inducible-signaling pathway protein 1, WNT1-inducible-signaling pathway protein 3, EGF-containing fibulin-like extracellular matrix protein 2, Low-density lipoprotein receptor, Pro-epidermal growth factor, Complement component C9, Thrombomodulin, Vitamin K-dependent protein S, Complement component C8 alpha chain, Uromodulin, Furin, Bone morphogenetic protein 1, Nidogen-1, Insulin receptor-related protein, Fibulin-1 and -2, Proprotein convertase subtilisin/kexin type 6, Connective tissue growth factor, Fibrillin-1, -2 and -3, Neurogenic locus notch homolog protein 1, Protein NOV homolog, CD97 antigen, Cartilage oligomeric matrix protein, Keratin, type II cuticular Hb3, Protein jagged-1, Protein crumbs homolog 1, Serine protease HTRA4, Serine protease HTRA3, Low-density lipoprotein receptor-related protein 2, Neurogenic locus notch homolog protein 2, Tumor necrosis factor receptor superfamily member 9, Prolow-density lipoprotein receptor-related protein 1, EGF-containing fibulin-like extracellular matrix protein 1, Nidogen-2, Scavenger receptor class F member 1, Adhesion G protein-coupled receptor E1, Growth arrest-specific protein 6, Keratin, type I cuticular Ha2, Latent-transforming growth factor beta-binding protein 1, Latent-transforming growth factor beta-binding protein 2, R-spondin-1, -2 and -4, Sushi, von Willebrand factor type A, EGF and pentraxin domain-containing protein 1, Uromodulin-like 1, Meckelin, Protein eyes shut homolog, Proprotein convertase subtilisin/kexin type 4, Sushi domain-containing protein 1, Cysteine-rich with EGF-like domain protein 2, Nephronectin, Protocadherin Fat 4, BMP/retinoic acid-inducible neural-specific protein 3, Extracellular matrix protein FRAS1, Epidermal growth factor-like protein 6, Signal peptide, CUB and EGF-like domain-containing protein 1, Signal peptide, CUB and EGF-like domain-containing protein 3, Latent-transforming growth factor beta-binding protein 4, Hemicentin-2, Delta and Notch-like epidermal growth factor-related receptor, Insulin-like growth factor-binding protein-like 1, Serine protease HTRA1, Proprotein convertase subtilisin/kexin type 5, Protein kinase C-binding protein NELL1, von Willebrand factor C and EGF domain-containing protein, Scavenger receptor class F member 2, Cysteine-rich with EGF-like domain protein 1, Kazal-type serine protease inhibitor domain-containing protein 1, Hemicentin-1, Protein kinase C-binding protein NELL2, Neurogenic locus notch homolog protein 4, R-spondin-3, Adhesion G protein-coupled receptor E3, Mucin-13, Endosialin, Cadherin EGF LAG seven-pass G-type receptor 2, Complement component C1q receptor, Endothelial cell-specific molecule 1, Signal peptide, CUB and EGF-like domain-containing protein 2, Delta-like protein 4, Latent-transforming growth factor beta-binding protein 3, Delta-like protein 3, Cadherin EGF LAG seven-pass G-type receptor 1, Low-density lipoprotein receptor-related protein 1B, Cysteine-rich motor neuron 1 protein, Fibulin-5, Epidermal growth factor-like protein 7, Adhesion G protein-coupled receptor E2, Neurogenic locus notch homolog protein 3, Protein jagged-2 and others.

Potential ligands of the IGFR-like receptor 2 described herein thus include ligands of the aforementioned proteins, such as IR, IGF1R, insulin, IGFR-I1, IGF1, IGF2, ephrin-B1, ephrin-B2, EGF, EGFR, TGFA/TGF-alpha, amphiregulin, epigen/EPGN, BTC/betacellulin, epiregulin/EREG, HBEGF/heparin-binding EGF, GP30, ALB, MB, Kappa and lambda-light chains, TF, hemoglobin, GC, SCGB1A1, APOA1, high density lipoprotein, the GIF-cobalamin complex, LRP2, LGALS3, AGRIN, IL-1, IL-2, TNF, collagen 1 and IV, perlecan, laminin, heparin, integrin, fibronectin, protein C, EFNA5, EFNB1, EFNB2, EFNB3, Jagged1, Jagged2 and Delta1, neuregulins, NTAK, CSPG5, TNFSF9/4-1BBL, Ac-LDL, AXL, TYRO3 MER, NRG1, NRG2, NRG3, NRG4, BTC, EREG, HBEGF, GR4, LGR5, LGR6, C1q, mannose-binding lectin (MBL2), pulmonary surfactant protein A (SPA), TGFBR2, and fragments and variants thereof.

Proteins comprising Mannose-6-phosphate receptor binding domain (InterPro Acc. No. IPR009011) include, without limitation, the cation-independent mannose-6-phosphate receptor, glucosidase 2 subunit β, the cation-dependent mannose-6-phosphate receptor, Protein OS-9, Endoplasmic reticulum lectin 1, and N-acetylglucosamine-1-phosphotransferase subunit gamma.

Potential ligands of the IGFR-like receptor 2 provided herein therefore include ligands of the aforementioned proteins, such as IGF2, DPP4, phosphomannosyl, TRPV4, IGF2, lysosomal enzymes, TGF β, Leukemia inhibitory factor (LIF), Proliferin, Thyroglobulin, Prorenin, Granzyme B, and Retonic Acid.

The present inventors found that knockdown or knockout of the IGFR-like receptor 2 resulted in increased phosphorylation of IGF1R and IR, and of downstream signaling protein Akt. Moreover, it could be observed that reduction of IGFR-like 2 levels leads to modulation of IGFR-like 1, suggesting that IGFR-like 2 regulates internalization, degradation or recycling of IGFR-like 1. It is thus supposed that the IGFR-like receptor 2 may inhibit or dampen IGF1R- and/or IR activation and/or downstream signaling. Without wishing to be bound by specific theory, it is thought that the IGFR-like receptor 2 similar as IGFR-like receptor 1 may for instance function as an "insulin scavenger" receptor depleting insulin from the blood and transferring it to the endo- and lysosomal compartments where it may be degraded. It is also speculated that the IGFR-like receptor 2 after interaction to the previously described IGFR-like receptor 1 may associate with the insulin receptor (InsR), resulting in removal of the InsR from the cell surface. Either way, these scenarios may explain decreased InsR activation and InsR and/or IGF1R-mediated signaling, including phosphorylation of InsR, IGF1R and/or Akt in the presence of functional IGFR-like receptors. Therefore, insulin, InsR and/or the insulin-IR complex are particularly envisaged as ligands for the IGFR-like receptor 2 provided herein.

Antagonists and Agonists

Further, agonists and antagonists of the IGFR-like receptor 2 described herein are provided. As described herein and demonstrated in the appended examples, the IGFR-like receptor 2 has been found to negatively regulate, i.e. inhibit or reduce InsR- and/or IGF1R-mediated signaling, and in particular Akt phosphorylation (see FIG. 11).

The term "antagonist" refers to receptor ligand that inhibits or reduces agonist-mediated biological responses rather than provoking a biological response itself upon binding to the receptor. Antagonists have affinity but essentially no efficacy for their receptors. The term also comprises antagonists binding to the active (orthosteric) or to allosteric sites of their receptors, and/or to other binding sites not normally involved in receptor function. The term "antagonist" in general comprises full and partial antagonists, reversible and irreversible antagonists. In accordance with the invention, the antagonist preferably specifically binds to the IGFR-like receptor 2.

The term "agonist" as used herein generally refers to a receptor ligand that activates the receptor upon binding to produce a biological response. In contrast to antagonists, agonists have both affinity and efficacy for their receptors. The term "agonist" in general comprises full and partial agonists, reversible and irreversible agonists. In accordance with the invention, the agonist preferably specifically binds to the IGFR-like receptor 2.

The "antagonist" or "agonist" of the present invention may in general be any molecule, such as an antibody, a siRNA, a nucleic acid, an aptamer, a peptide, a protein, or a small molecule organic compound, that binds or specifically binds to an IGFR-like receptor 2 as specified herein, or a variant or a fragment thereof, and either blocks or reduces the biological responses mediated by the IGFR-like receptor 2 (i.e. acts as an antagonist) or induces or increases the biological responses mediated by the IGFR-like receptor 2 (i.e. acts as an agonist).

Agonists and antagonists of the IGFR-like receptor 2 can be easily found e.g. using the screening assay as provided herein. The skilled person will readily acknowledge that ligands of proteins comprising e.g. an insulin-like growth factor binding domain and/or a mannose-6-phosphate receptor binding domain (exemplary proteins and ligands have been described in the "Ligands" section above) may be used as a template for preparing agents capable of binding to the IGFR-like receptor 2 and exhibiting an agonistic or antagonistic effect. E.g., in case of protein or peptide ligands, variants and fragments thereof can be easily prepared using routine methods of genetic engineering. The agonists and antagonists of the invention are envisaged to specifically bind to the IGFR-like receptor 2 described herein (i.e. preferably do not exhibit cross-reactivity towards targets other than the IGFR-like receptor 2), as can easily be tested e.g. by evaluating antibody binding in IGFR-like receptor 2 knockdown host cells.

Antibody

The antagonist or agonist provided herein may be an antibody. The antibodies provided herein preferably exhibit the desired biological activity, i.e. specifically bind to the IGFR-like receptor 2 described herein. It is thus also envisaged that the antibodies of the invention targeting IGFR-like receptor 2 interfere with receptor homo- and heterodimerization of IGFR-I1 and IGFR-I2 and/or ligand binding. Accordingly, an antibody may reduce formation of an IGFR-I1/IGFR-I2 protein complex or formation of an IGFR-I2/IGFR-I2 protein complex.

Also envisaged herein are antibodies which may reduce formation of an IGFR-I1/IGFR-I1 protein complex or formation of an IGFR-I1/InsR or IGFR-I1/IGF-1R complex.

Specifically, it is envisaged that the antagonistic antibodies of the invention are capable of increasing InsR and/or IGF1R-mediated signaling, and in particular phosphorylation of Akt and/or other downstream signaling components that becomes active when either IGFRs or InsR or both transmit a signal, as ascertainable using routine methods known in the art and described in the appended examples. "Increase" thereby denotes an increase in the respective signal in the presence of the antibody when compared to the absence of the antibody in the respective detection method which is used for the detection and/or quantification of said increase. Strikingly, IGFR-I contains an extracellular domain that shows great similarity to the HER2 dimerization region, which is targeted by the antibody trastuzumab (Herceptin®). HER2 is constitutively active being able to dimerize with other HER family members acting in a ligand-independent manner and targeting HER2 by trastuzumab blocks its activity and inhibits cancer growth. Moreover, IGFR-I and IGFR-I2 contain a GxxxG dimerization motif in its transmembrane domain that is found in members of the EGFR family. This suggests that IGFR-I homo- and heterodimerizes with EGFR and IR family members to regulate cell signaling outcome, metabolic vs mitogenic. It is thus also envisaged that the antibodies of the invention targeting IGFR-like receptor 2 interfere with receptor homo- and heterodimerization and/or ligand binding.

Methods to provide such antibodies are well known to the skilled person (e.g. WO/2014/124020) and exemplified hereinafter. One may purify the IGFR-I2 ectodomain (also referred to herein as extracellular domain) as well as the full-length receptor to high purity using a mammalian expression system to generate fully N-glycosylated, properly folded receptor with native conformation. Receptor reconstitution in synthetic membranes not only allows for dimerization of the receptor within a lipid bilayer, but also presents the receptor as an antigen in the membrane context and thus is highly suitable for the generation of the antibodies of the present invention and in particular f the therapeutic antibodies of the invention. Thus IGFR-I2 proteoliposomes are a synthetic mimic of the cellular membranes and thus ideal to produce e.g. monoclonal. These antibodies are directed against the extracellular domain of the receptor only and may interfere with receptor homo- and heterodimerization and/or ligand binding. It is thus also envisaged that the antibodies of the invention are capable of binding to the glycosylated IGFR-like receptor 2, preferably to its glycosylated ectodomain.

As is well known in the art, an antibody is an immunoglobulin molecule capable of specific binding to a target (epitope) through at least one epitope recognition site, located in the variable region of the immunoglobulin molecule. The term "antibody" as used herein comprises monoclonal and polyclonal antibodies, as well as (naturally occurring or synthetic) fragments or variants thereof, including fusion proteins comprising an antibody portion with an antigen-binding fragment of the required specificity and any other modified configuration of the antibody that comprises an antigen-binding site or fragment (epitope recognition site) of the required specificity. Illustrative examples include dAb, nanobody, affibody, Fab, Fab', F(ab')$_2$, Fv, single chain Fvs (scFv), diabodies, and minibodies comprising a scFv joined to a CH3 domain. It will be understood that other antibody frameworks or scaffolds comprising "antigen-binding sites" can be employed in line with the present invention. The term "antibody" thus also comprises these scaffolds. The mentioned scaffolds include e.g. non-immunoglobulin based antibodies and scaffolds onto which CDRs of the antibodies can be grafted. Such scaffolds include for example anticalins, avimers, affilins etc.

The antibody may be a chimeric antibody (or antigen-binding variant or fragment thereof). The term "chimeric antibody" refers to an antibody in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies.

The antibody may be a humanized antibody (or antigen-binding variant or fragment thereof). The term "humanized antibody" refers to an antibody containing a minimal sequence derived from a non-human antibody. In general, humanized antibodies are human immunoglobulins comprising residues from a hypervariable region of an immunoglobulin derived from non-human species such as mouse, rat, rabbit or non-human primate ("donor antibody") grafted onto the human immunoglobulin ("recipient antibody"). In some instances, framework region (FR) residues of the human immunoglobulin are replaced by corresponding non-human residues. Furthermore, humanized antibodies may comprise residues that are neither found in the recipient antibody nor in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

The antibody may be a human antibody. A "human antibody" is one that possesses an amino-acid sequence corresponding to that of an antibody produced by a human and/or has been made using any of the techniques for making human antibodies. This definition of a human antibody specifically excludes a humanized antibody comprising non-human antigen-binding residues. Human antibodies can be produced using various techniques known in the art, including phage-display libraries (Hoogenboom and Winter, J. Mol Biol, 227:381 (1991); Marks et al, J. Mol Biol, 222:581 (1991)). Also available for the preparation of human monoclonal antibodies are methods described in Cole et al, Monoclonal Antibodies and Cancer Therapy, Alan R. Liss, p. 77 (1985) and Boerner et al., J. Immunol, 147W:86-95 (1991). See also van Dijk and van de Winkel, Curr. Opin. Pharmacol, 5: 368-374 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-

3562 (2006) regarding human antibodies generated via a human B-cell hybridoma technology.

Chemical Modifications

The antibodies or antigen-binding variants or fragments thereof used in accordance with of the invention may be modified. Typical modifications conceivable in the context of the invention include, e.g., chemical modifications as described in the following.

Generally, all kind of modifications are conceivable as long as they do not abolish the capability of the antibodies or antigen-binding variants or fragments thereof to specifically bind to the IGFR-like receptor 2 and act as antagonists or agonists of the IGFR-like receptor 2 as described elsewhere herein.

Possible chemical modifications of the antibody or antigen-binding variants or fragments thereof include acylation or acetylation of the amino-terminal end or amidation or esterification of the carboxy-terminal end or, alternatively, on both. The modifications may also affect the amino group in the side chain of lysine or the hydroxyl group of threonine. Other suitable modifications include, e.g., extension of an amino group with polypeptide chains of varying length (e.g., XTEN technology or PASylation®), N-glycosylation, O-glycosylation, and chemical conjugation of carbohydrates, such as hydroxyethyl starch (e.g., HESylation®) or polysialic acid (e.g., PolyXen® technology). Chemical modifications such as alkylation (e. g., methylation, propylation, butylation), arylation, and etherification may be possible and are also envisaged.

As described elsewhere herein, several domains have been identified in the IGFR-like receptor 2 of the invention. Antibodies acting as antagonists or agonists of the IGFR-like receptor 2 are in principle envisaged to bind anywhere in, or in between, the preferably extracellular domains of the IGFR-like receptor 2 as described herein. As such, known antibodies binding to proteins comprising one or more of said domains, are generally also envisaged as antagonists or agonists and can be easily monitored for their antagonistic or agonistic behavior in the screening assay provided herein.

Further, antibodies against the IGFR-like receptor 2 can be prepared as described herein and tested for their agonistic or antagonistic activity as described herein.

The antibodies provided as antagonists or agonists in accordance with the present invention are in particular envisaged to be capable of binding to an IGFR-like receptor 2 epitope within the extracellular domain of IGFR-I2 as shown in SEQ ID NO: 2.

The antibodies preferably bind to the IGFR-like receptor 2 described herein specifically, i.e. not to exhibit cross-reactivity towards non-target molecules such as IGFR-I1, InsR, the IGF1R and IGF2R.

The term "epitope" in general refers to a site on an antigen to which a binding domain, such as an antibody or immunoglobulin or derivative or fragment of an antibody or of an immunoglobulin, specifically binds. An "epitope" is antigenic and thus the term epitope is sometimes also referred to herein as "antigenic structure" or "antigenic determinant". Thus, the binding domain is an "antigen interaction site". Said binding/interaction is also understood to define a "specific recognition". The term "epitope" encompasses linear epitopes and conformational epitopes. Linear epitopes are contiguous epitopes comprised in the amino acid primary sequence and typically include at least 3 or at least 4, and more usually, at least 5 or at least 6 or at least 7, for example, about 8 to about 10 amino acids in a unique sequence. Conformational epitopes are formed by non-contiguous amino acids juxtaposed by folding of the protein. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

Other molecules are also envisaged herein as antagonists or agonists of the IGFR-like receptor 2.

siRNAs and nucleic acids are particularly useful as IGFR-like receptor 2 antagonists that reduce or inhibit expression of IGFR-I2 gene as shown in SEQ ID NO: 1 (or variants or orthologs thereof). The term "siRNA" is used interchangeably with "small interfering RNA" or "silencing RNA". siRNAs are double-stranded "antisense" RNA molecules, typically including a sequence of at least 20 consecutive nucleotides having at least 95% sequence identity to the complement of the sequence of the target nucleic acid, such as the coding sequence of the IGFR-I2 gene, but may as well be directed to regulatory sequences of said gene, including the promoter sequences and transcription termination and polyadenylation signals.

Other nucleic acids capable of reducing and/or inhibiting IGFR-like receptor 2 expression include aptamers, Spiegelmers®, nc-RNAs (including anti-sense-RNAs, L-RNA Spiegelmer, silencer RNAs, micro-RNAs (miRNAs), short hairpin RNAs (shRNAs), small interfering RNAs (siRNAs), repeat-associated small interfering RNA (rasiRNA), and molecules or an RNAs that interact with Piwi proteins (piRNA). Such non-coding nucleic acid molecules can for instance be employed to direct IGFR-like receptor 2 mRNA degradation or disrupt IGFR-like receptor 2 mRNA translation. A respective reactant, in particular siRNA molecule, may in principle be directly synthesized within the host cell, or may be introduced into the host cell.

Peptides and proteins can in general be employed as IGFR-receptor 2 antagonists or agonists, depending on whether they suppress (antagonists) or evoke (agonists) the biological responses mediated by IGFR-like receptor 2 signaling. The term "polypeptide" and "protein" are used interchangeably herein. It is envisaged that proteins and peptides bind specifically to the IGFR-like receptor 2. As set out previously herein, the skilled person will readily be able to find peptide and protein antagonists or agonists capable of specifically binding to the IGFR-like receptor 2. Small organic molecules are, too, capable of either acting as IGFR-like receptor 2 antagonists or agonists. It is envisaged that small organic molecules specifically bind to the IGFR-like receptor 2. High-throughput screening assays for small organic molecules are readily available in the art and can be employed to find ligands of the IGFR-like receptor 2 provided herein that may exhibit agonistic or antagonistic activity.

Specific Binding

As set out herein, specific binding of the binding agents, in particular antagonists and agonists provided herein, e.g. antibodies, to the IGFR-like receptor 2 is preferred. The terms "binding to" and "recognizing" in all grammatical forms are used interchangeably herein.

The term "specifically binds" generally indicates that a binding agent, in particular an antagonist or agonist, such as an antibody, binds with higher affinity to its intended target (i.e. the IGFR-like receptor 2 described herein) than to its non-target molecule. Non-target molecules include the IGF receptors, in particular IGFR-I1, the human IGF1R with Uniprot Acc. No. P08069 (entry version 185 of 22 Jul. 2015), the human IGF2R with Uniprot Acc. No. P11717 (entry version 174 of 22 Jul. 2015), and the human InsR with Uniprot Acc. No. P06213 (entry version 216 of 22 Jul.

2015); and functional variants thereof. Preferably the affinity of the agonist or antagonist will be at least about 5 fold, preferably 10 fold, more preferably 25-fold, even more preferably 50-fold, and most preferably 100-fold or more, greater for a target molecule than its affinity for a non-target molecule. Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Preferably, the term "specifically binds" thus indicates that an antagonist or agonist, such as an antibody, exclusively binds to its intended target (i.e., the IGFR-like receptor 2).

Treatment

It is envisaged that the IGFR-like receptor 2 antagonists and agonists are particularly useful in treatment and diagnostic of cancer and diabetes. As used herein, "cancer" refers to all disorders associated with uncontrolled cell proliferation in any tissue, and particularly comprises endometrial cancer, gastric cancer, breast cancer, prostate cancer, lung cancer, and/or brain cancer (in particular pituitary gland cancer). The term "diabetes" as used herein refers to the broad class of disorders characterized by impaired insulin production and glucose tolerance and in general includes type 1 and type 2 diabetes (also called juvenile and adult-onset, respectively), gestational diabetes, prediabetes, insulin resistance, metabolic syndrome, and impaired glucose tolerance. Diabetes results from a deficiency or functional impairment of insulin-producing β cells, alone or in combination with insulin resistance.

The term "metabolic syndrome" comprises abdominal (central) obesity, elevated blood pressure, elevated fasting plasma glucose, high serum triglycerides, low high-density lipoprotein (HDL) and/or high low-density lipoprotein (LDL) levels. Further it is associated with the risk of developing type 2 diabetes and/or cardiovascular disease including coronary heart diseases.

The term "β cell(s)", "beta cell(s)" and "islet cell(s)" are used interchangeably herein to refer to the pancreatic β cells located in the islet of Langerhans. Their primary function is to store and release insulin.

Defective insulin secretion underlies all forms of diabetes mellitus. Whereas the destruction of β-cells is responsible for type 1 diabetes (T1D), both lowered β-cell mass and loss of secretory function are implicated in type 2 diabetes (T2D). Emerging results suggest that a functional deficiency, involving de-differentiation of the mature β-cell towards a more progenitor-like state, may be an important driver for impaired secretion in T2D.

It is contemplated that the antagonists and agonists of the present invention can advantageously be employed in preventing β cell de-differentiation and/or reverting β cell loss-of-function. The antagonist and agonists described herein are therefore envisaged for use as a medicament. Particularly, said antagonists and agonists are intended for use in a method of prophylactic and/or therapeutic treatment of diabetes. Further, the use of said antagonists and agonists for the manufacture of a medicament for therapeutic application in diabetes or cancer is also contemplated by the present invention.

Type 1 diabetes is also known as Insulin Dependent Diabetes Mellitus (IDDM), and juvenile diabetes. The terms are used interchangeably herein. This form accounts for 5-10% of diabetes and is thought to be due to cellular-mediated autoimmune destruction of the pancreatic β-cells, resulting in little or no insulin secretion. Antagonists and agonists of the IGFR-like receptor 2 provided herein may be capable of preventing or even reverting β cell de-differentiation and/or loss-of-function. Thus, the present invention is envisaged to open up new possibilities for a preventive or regenerative therapy of T1D.

Type 2 diabetes is also referred to as adult-onset diabetes and accounts for ~90-95% of all diabetes. Insulin resistance in target tissues and a relative deficiency of insulin secretion from pancreatic β-cells are the major features of type 2 diabetes (T2D). Insulin resistance is used herein to denote a condition characterized by the failure of target cells to respond to insulin, leading to hyperglycemia. Pancreatic β cells in the pancreas subsequently increase their production of insulin, leading to hyperinsulinemia.

As further shown in the appended examples, the present inventors demonstrated that the IGFR-like receptor 2 described herein negatively regulates insulin downstream signaling. IGFR-like receptor 2 antagonists are therefore envisaged to promote or restore InsR downstream signaling, whereas IGFR-like receptor 2 agonists are thought to inhibit or dampen InsR signaling. IGFR-like receptor 2 antagonists are therefore preferably capable of increasing InsR and/or IGF1R-mediated Akt phosphorylation and/or increasing InsR and/or IGF1R-mediated phosphorylation of other downstream signaling components that become active when either IGFRs or InsR or both transmit a signal, thereby advantageously increasing insulin sensitivity in insulin-resistant cells.

Diagnostics

The present invention further provides a binding molecule capable of specifically binding to an IGFR-like receptor 2 as described herein for use as a diagnostic marker for diabetes or the risk of developing diabetes. Preferably, said IGFR-like receptor 2 comprises a sequence corresponding to sequence SEQ ID No 2, however, variants of said IGFR-like receptor 2 are also envisaged.

In general, in order to provide a diagnostic binding agent, the skilled person may follow the same principles as set out in the context of providing antagonists and agonists of the IGFR-like receptor 2. Likewise, diagnostic binding agents provided herein are envisaged to specifically bind to the IGFR-like receptor 2 provided herein. Diagnostic binding agents may exhibit antagonistic or agonistic activities (thereby e.g. enabling simultaneous diagnosis and (preventive) treatment, or may not have an effect on IGFR-like receptor 2 signaling at all.

Particularly useful binding agents for use within the in vitro diagnostic binding assay comprise monoclonal antibodies, e.g. antibodies specifically recognizing an IGFR-like receptor 2 epitope, preferably within its extracellular domain.

The diagnostic binding agents employed in the methods of the invention may further comprise a detectable label attached to the diagnostic binding agent. The detectable label may be (preferably covalently) attached to the diagnostic binding agents either directly or via spacers of various lengths to reduce potential steric hindrance. Various methods for labelling proteins are known in the art and can be used in performing the present invention. The term "label" or "labelling group" refers to any detectable label. Suitable labels for use in with the diagnostic binding agent include, without limitation, (i) isotopic labels, which may be radioactive or heavy isotopes, such as radioisotopes or radionuclides (e.g., $^{3}H$, $^{14}C$, $^{15}N$, $^{35}S$, $^{89}Zr$, $^{90}Y$, $^{99}Tc$, $^{111}In$, $^{125}I$, $^{131}I$), (ii) magnetic labels (e.g., magnetic particles), (iii) redox active moieties, (iv) optical dyes (including, but not limited to, chromophores, phosphors and fluorophores) such as fluorescent labels (e.g., FITC, rhodamine, lanthanide phosphors), chemiluminescent labels, and fluorophores which can be either "small molecule" fluorophores or proteinaceous fluorophores, (v) enzymatic groups (e.g. horseradish peroxidase, β galactosidase, luciferase, alkaline phosphatase), (vi) biotinylated groups, (vii) predetermined polypeptide epitopes recognized by a secondary reporter (e.g., leucine zipper pair sequences, binding sites for secondary antibodies, metal binding domains, epitope tags, etc.).

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, OR), FITC, Rhodamine, and Texas Red (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland. Exemplary proteinaceous fluorescent labels also include, but are not limited to, green fluorescent protein, including a Renilla, Ptilosarcus, or Aequorea species of GFP, EGFP, blue fluorescent protein (BFP), enhanced yellow fluorescent protein (EYFP), luciferase, and β galactosidase.

It is within the knowledge of the skilled person to choose a suitable label depending on the type of diagnostic binding agent, its chemical properties and intended detection method. Particularly suitable diagnostic binding agents for use in the methods of the invention are monoclonal antibodies, preferably specifically recognizing the IGFR-like receptor 2 described herein.

Patients

The term "patient" or "subject" as used herein refers to a human or non-human animal, generally a mammal. Particularly envisaged is a mammal, such as a rabbit, a mouse, a rat, a Guinea pig, a hamster, a dog, a cat, a pig, a cow, a goat, a sheep, a horse, a monkey, an ape or preferably a human. Thus, the methods, uses and compounds described in this document are in general applicable to both human and veterinary disease.

Treatment

The term "treatment" in all its grammatical forms includes therapeutic or prophylactic treatment. A "therapeutic or prophylactic treatment" comprises prophylactic treatments aimed at the complete prevention of clinical and/or pathological manifestations or therapeutic treatment aimed at amelioration or remission of clinical and/or pathological manifestations of the diseases. The term "treatment" thus also includes the amelioration or prevention of diabetes.

In the context with the present invention the term "therapeutic effect" in general refers to the desirable or beneficial impact of a treatment, e.g. amelioration or remission of the disease manifestations. The term "manifestation" of a disease is used herein to describe its perceptible expression, and includes both clinical manifestations, hereinafter defined as indications of the disease that may be detected during a physical examination and/or that are perceptible by the patient (i.e., symptoms), and pathological manifestations, meaning expressions of the disease on the cellular and molecular level. The therapeutic effect of treatment with the IGFR-I2 antagonists and agonists can be assessed using routine methods in the art, e.g. measuring insulin levels and/or glucose levels in blood samples of the patient. Additionally or alternatively it is also possible to evaluate the general appearance of the respective patient (e.g., fitness, well-being) which will also aid the skilled practitioner to evaluate whether a therapeutic effect has been elicited. The skilled person is aware of numerous other ways which are suitable to observe a therapeutic effect of the compounds of the present invention.

Dose

Preferably, a therapeutically effective amount of the compound as described herein is administered. By "therapeutically effective amount" is meant an amount of the compound as described herein that elicits a therapeutic effect. The exact dose of IGFR-like receptor 2 antagonists or agonists will depend on the purpose of the treatment (e.g. remission maintenance vs. treatment of acute flare of the disease), and will be ascertainable by one skilled in the art using known techniques. Adjustments for route of administration, age, body weight, general health, sex, diet, time of administration, drug interaction and the severity of the condition may be necessary, and will be ascertainable with routine experimentation by those skilled in the art.

Administration

A variety of routes are applicable for administration of the compound according to the present invention, including, but not limited to, orally, topically, transdermally, subcutaneously, intravenously, intraperitoneally, intramuscularly or intraocularly. However, any other route may readily be chosen by the person skilled in the art if desired.

Composition

It is envisaged to administer the IGFR-I2 antagonists or agonists in the form of a pharmaceutical composition. Preferably, said antagonists or agonists are present in the pharmaceutical composition in a therapeutically effective amount. Particularly preferred antagonists or agonists for use in the pharmaceutical composition provided herein are monoclonal antibodies specifically binding to the IGFR-like receptor 2 described herein.

The term "pharmaceutical composition" particularly refers to a composition suitable for administering to a human, i.e., a composition that is preferably sterile and/or contains components which are pharmaceutically acceptable. However, compositions suitable for administration to non-human animals are also envisaged herein. Preferably, a pharmaceutical composition comprises an IGFR-I2 antagonist or agonist together with one or more pharmaceutical excipients. The term "excipient" includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers or tonicity modifiers. Pharmaceutical compositions of the invention can be formulated in various forms, e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration.

The pharmaceutical composition of the present invention may further comprise one or more additional agents. Preferably, said agents are therapeutically effective for treatment the diseases described herein and present in the composition in a therapeutically effective amount.

In view of the above, the present invention hence also provides a pharmaceutical composition comprising an IGFR-I2 antagonist or agonist. Said pharmaceutical composition is particularly intended for use in a method of therapeutic and/or prophylactic treatment of diabetes or cancer.

Kit

A kit is also provided herein. The kit may be a kit of two or more parts, and comprises the IGFR-like receptor 2 antagonist or agonist, preferably in a therapeutically effective amount and in a pharmaceutically acceptable form. The components of the kit may be contained in a container or vials. The kit is envisaged to comprise additional agents useful in treating diabetes or cancer, as described elsewhere herein.

The IGFR-I2 antagonist or agonist and the additional agents can be administered simultaneously or sequentially to the patient.

Screening Assay

When used herein the term "screening assay" is equivalently used with the term "screening method". Such assay or method is preferably performed "in vitro". However, it can also be performed "in vivo".

Antagonists and agonists of the IGFR-like receptor 2 can be identified using an in vitro screening assay as provided herein, said assay comprises the following steps: (a) providing a stable cell line expressing said IGFR-like receptor 2; (b) contacting said cell line of (a) with a candidate antagonist or agonist; and (c) measuring an IGFR-like receptor 2 downstream signaling event, wherein an antagonist is identified by increasing said IGFR-like receptor 2 downstream signaling event, and an agonist is identified by decreasing said IGFR-like receptor 2 downstream signaling event; wherein said IGFR-like receptor 2 comprises a sequence corresponding to sequence SEQ ID No. 2.

Optionally, in the herein described screening methods, a cell line, preferably the same cell line as is applied in the screening methods of the present invention, expressing said IGFR-like receptor 2 is not contacted with a candidate antagonist or agonist, respectively. Such cell line serves as control. In such a control cell line also an IGFR-like receptor 2 downstream signaling event is measured and compared to the IGFR-like receptor 2 downstream signaling event measured in a cell line that is (or was) contacted with a candidate antagonist or agonist.

IGFR-like receptor 2 expression is preferably in the pancreas, in pancreatic β-cells. Expression may also be detected in the pituitary gland (e.g. hormone-producing cells). This may implicate an important role of IGFR-like receptor 2 in the regulation of the hypothalamic-pituitary-gonadal (HPG) axis, which controls growth and metabolism. Further, expression may also be detected in breast cancer (e.g. MCF7 cell line).

Additionally, both receptors, IGFR-like receptor 1 and 2 may be expressed simultaneously in cells, such as in pancreatic β-cells.

Preferred examples of cell lines expressing said IGFR-like receptor 2 comprise Min6 or PDX1+/NKX6.1+iPSC.

As described herein, IGFR-like receptor 2 downstream signaling events are thought to result in a negative regulation of InsR- and/or IGF1R-mediated signaling, and in particular in inhibited or reduced Akt phosphorylation, and/or inhibited or reduced phosphorylation of other downstream signaling components that become active when either IGFRs or InsR or both transmit a signal. As such, a binding agent promoting or increasing Akt phosphorylation, and/or phosphorylation of other downstream signaling components that become active when either IGFRs or InsR or both transmit a signal, in the screening assay provided herein is likely an antagonist of the IGFR-like receptor 2. A binding agent not having any effect on or even reducing Akt phosphorylation, and/or on reducing phosphorylation of other downstream signaling components that become active when either IGFRs or InsR or both transmit a signal, in the screening assay provided herein is likely an agonist of the IGFR-like receptor.

The stable cell line may be any cell line suitable for expressing a functional IGFR-like receptor 2, wherein a "functional IGFR-like receptor 2" is particularly envisaged to bind or interact with IGFR-I1 as described herein elsewhere.

The invention also relates to an antagonist or agonist obtainable by the screening method.

The present invention also contemplates a method for detecting whether IGFR-like receptor 2 homo- or heterodimerizes with IGFR-I1, IGFR-I1, IGFR-2 and/or InsR. Said method comprises detecting whether a tagged IGFR-like receptor 2 homodimerizes or heterodimerizes. Heterodimers may include the IGFR-I2 with IGFR-I1, or IGFR-I2 with any of InsR, IGFR-I1 and/or IGF-R2.

Preferred tags are fluorescent proteins, such as GFP or Venus, a genetic mutant of green fluorescent protein (GFP) with an emission peak of 527 nm.

Tagging the IGFR-like receptor 2 is preferably achieved by fusing a tag in frame to said IGFR-like receptor 2. This may be achieved by techniques known in the art, e.g. by knocking-in the nucleotide sequence encoding said IGFR-like receptor 2 a nucleotide sequence encoding a tag, e.g. by genome editing, such as using the CRIPSR/Cas system.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., "about 20" includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be had from the following examples, offered for illustrative purposes only. The examples are not intended to limit the scope of the present invention in any way.

EXAMPLES

Material and Methods

Example 1: Generation of the IGFR-Like Receptor Knockout Mice

All mice were housed in the central facilities at HMGU in accordance with the German animal welfare legislation and acknowledged guidelines of the Society of Laboratory Animals (GV-SOLAS) and of the Federation of Laboratory Animal Science Associations (FELASA). Sacrifice of mice at embryonic stages was not subject to regulatory authorization.

Targeted ES cell clones derived from C57BL/6N parental cell line JM8.N4 were obtained from the EUCOMM cell repository (EuMMCR) (Helmholtz Zentrum Muenchen GmbH, Alleles produced for the EUCOMM and EUCOMMTools projects by the Helmholtz Zentrum Muenchen GmbH (Hmgu). MGI Direct Data Submission. 2010-2015) and were injected into CD1 blastocysts for chimera generation. The resulting chimeras were mated to CD1 or C57BL/6J mice, and the progeny were screened by PCR to confirm germline transmission. Heterozygous mice carrying the targeted mutation were intercrossed to generate homozygous mutant mice either in CD1 or C57BL/6J background.

Genotyping was confirmed by PCR using genomic DNA extracted from the tails of control and knockout mice.

Example 2: Proliferation Assay

To assess cell proliferation in mutant embryos the pregnant females were injected subcutaneously with 0.1 mg EdU/gram body weight. After two hours, the animals were sacrificed and pancreata from E14.5, E16.5 and E18.5 embryos were dissected and fixed in 4% PFA in PBS pH7.4 overnight at 4° C. Next day the organs were subjected to a 7.5%, 15%, 30% sucrose gradient embedded in Tissue Freezing Medium (Leica, Germany) and stored at −80° C. 20 micrometer cryosections were stained using Click-iT® EdU Imaging Kit (Life Technology) according to the manufacturer's instructions including antibodies against Insulin (1:250 guinea pig Thermo Schientific; PA1-26938). Images were acquired using a Leica SP5 Confocal microscope with a 20× objective and data analysis was performed using IMARIS software (Bitplane, Switzerland).

Example 3: RT-qPCR

For gene expression analysis, by real time quantitative PCR, mRNA was isolated from pancreata of knockout and control embryos using miRNeasy mini kit (Qiagen, Germany). The cDNA was synthesized using GoScript™ Reverse Transcription System (Promega) and subsequently used for qPCR using TaqMan® Low Density Arrays and run on a ViiA 7 system (Applied Biosystems). The probes used are listed in table 1:

TABLE 1

| Gene symbol | Probe |
| --- | --- |
| Slc2a2 | Mm00446229_m1 |
| Slc30a8 | Mm00555793_m1 |
| Ucn3 | Mm00453206_s1 |
| Gjd3 | Mm00731344_s1 |
| Kcnj11 | Mm00440050_s1 |
| Abcc8 | Mm00803450_m1 |
| Smarca1 | Mm00474150_m1 |
| Mafa | Mm00845206_s1 |
| Mafb | Mm00627481_s1 |
| Foxa2 | Mm01976556_s1 |
| 18S | Hs99999901_s1 |
| Nkx2-2 | Mm00839794_m1 |
| Nkx6-1 | Mm00454962_m1 |
| Pax6 | Mm00443081_m1 |
| Pdx1 | Mm00435565_m1 |
| Neurod1 | Mm01946604_s1 |
| Glp1r | Mm00445292_m1 |
| Gcgr | Mm00433546_m1 |
| Gipr | Mm01316344_m1 |
| Prlr- | Mm00599957_m1 |
| Insr | Mm01211875_m1 |
| Insrr | Mm00442243_m1 |
| B9d1 | Mm00840045_m1 |
| Il6ra | Mm00439653_m1 |
| Cntfr | Mm00516693_m1 |
| Ffar1 | Mm00809442_s1 |
| Lgals3bp | Mm00478303_m1 |
| Sstr3 | Mm00436695_s1 |
| 1700009P17Rik | Mm00512620_m1 |
| Pard6a | Mm01247370_g1 |
| Atf2 | Mm00833804_g1 |
| Dvl3 | Mm00432914_m1 |
| Fzd3 | Mm00445423_m1 |
| Rhoa | Mm00834507_g1 |
| Rock1 | Mm00485745_m1 |
| Rock2 | Mm01270843_m1 |
| Wnt5b | Mm01183986_m1 |
| Gck | Mm00439129_m1 |
| Pcsk1 | Mm00479023_m1 |
| Pcsk2 | Mm00500981_m1 |
| Ccnd1 | Mm00432359_m1 |
| Ccnd2 | Mm00438070_m1 |
| Cdk4 | Mm00726334_s1 |
| Cdkn1a | Mm04205640_g1 |
| Cdkn1b | Mm00438168_m1 |
| Actb | Mm00607939_s1 |
| Rplp0 | Mm00725448_s1 |

Generation of Monoclonal Antibody against Estrogen-induced gene 121 protein (EIG).

Peptides from human EIG protein were synthesized and coupled to OVA (Peps4LS, Heidelberg, Germany). Lou/c rats or C57BL/6 mice were immunized subcutaneously and intraperitoneally with a mixture of 50 μg peptide-OVA, 5 nmol CPG oligonucleotide (Tib Molbiol, Berlin), 500 µl (mouse 100 µl) PBS and 500 µl (mouse 100 µl) incomplete Freund's adjuvant. A boost without adjuvant was given six weeks after the primary injection. Fusion was performed using standard procedures. Supernatants were tested in a differential ELISA with the biotinylated EIG peptides and an irrelevant biotinylated peptide on avidin coated ELISA plates. MAbs that reacted specifically with the EIG peptide were further analysed in Western blot.

Example 4: Cell Culture

Min6 is a pancreatic β-cell line which is well characterized for their ability to secret insulin upon glucose stimulation. This cell line was from Susumu Seino's Lab.

Min6 cells were maintained in high glucose Dulbecco's modified Eagle medium of Gibco (41966-052) supplemented with 10% fetal bovine serum (FBS), 1% Penicillin/ Streptomycin and 2-mercaptoethanol.

Example 5: IGFR-Like Receptor Knock-Down

Min6 cells were seeded at a cell density of $5 \times 10^4$ cells/$cm^2$ and cultured in high glucose DMEM medium. After one transfection of IGFR-like receptor siRNA at day two and day three, cells were lysed in RIPA buffer on ice at day 4 at a cell density of 50-60%. The lipofectamin (Lipofectamine 2000, Life Technologies, #11668019) based transfection was performed according to the protocol of Life Technologies and 200 pmol of following siRNA from Dharmacon GE Healthcare were used: On-Target plus mouse 5330417C22Rik (229722) siRNA-SMARTpool L-048745-01-0020 and control siRNA On-target plus non-targeting siRNA #1 D-001810-01-20.

Example 6: IGFR-Like Receptor Knock-Out

CRISPR/Cas9-mediated single IGFR-I knock-out (SKO) and double KO strategy in Min6 cells that targets transcriptional start codons (ATG).

Example 7: Starvation Assay Min6

Min6 cells were seeded at a cell density of $5 \times 10^4$ cells/$cm^2$ and cultured in high glucose DMEM medium. After performing a IGFR-like receptor knock-down Min6 cells were washed six times with 1×PBS and HBSS buffer containing 0.2% BSA was added for 15 min, 30 min, 60 min and 120 min to starve the cells. Subsequently, cells were lysed in RIPA buffer on ice.

Example 8: Western Blot (Semi-Dry Immunoblotting)

Cells and tissues were lysed in RIPA buffer (50 mM Tris pH7.5, 150 mM NaCl, 1 mM EDTA, 1% IGEPAL, 0.1% SDS, 0.1% Na deoxycholate) containing a cocktail of proteinase inhibitor (1:100, Sigma, P8340) and phosphatases inhibitors (1:100, Sigma Aldrich, #2 P0044 and #3 P5726) and the cell or tissue lysates were cleared by centrifugation at 13000 r.p.m. for 10-30 min. The proteins (10-20 µg) were resolved in 6.5-15% SDS-PAGE according to the protein size to be detected and transferred to a PVDF membrane. Primary antibodies were added to the membrane in 5% milk and incubated at 4° C. overnight. Protein bands were visualized on Hyperfilms (GE healthcare, 28906837) or Blaufilme CEA-RP (Ernst Christiansen GmbH, EC84A) by chemiluminescent detection (ECL, Millipore, WBKLS0500).

The following antibodies were used with corresponding dilutions:

IGFR-like receptor SEQ ID No. 2 (1:5000 rabbit Pineda, Berlin, Germany), IGFR-like receptor SEQ ID No. 2 (1:100 rat and mouse), IGFR-like receptor SEQ ID No. 4 and 6 (1:10 rat and mouse), Akt (1:5000 Cell Signaling, 4691), P-Akt (1:5000 Cell Signaling, 4060), Erk (1:5000 Cell Signaling, 4695), P-Erk (1:5000 Cell Signaling, 4370), m-Tor (1:1000 Cell Signaling, 2972), P-mTor (1:1000 Cell Signaling, 5536), Ampk (1:1000 Cell Signaling, 2532), P-Ampk (1:2500 Cell Signaling, 2535), IRS-2 (1:1000 Cell Signaling, 4502), IRβ (1:1000 Cell Signaling, 3025), S6rp (1:5000 Cell Signaling, 2217S), P-S6RP (1:5000 Cell Signaling, 2211S), P-IR/IGFR (1:1000, Millipore, 07-841), α-Tubulin (1:5000, Sigma, T7451), mouse Adaptin beta clone 74 (1:5000, BD Bioscience 610382). For the detection of autophagy related proteins the Autophagy Antibody Sampler Kit (#4445, 1:1000) of Cell Signaling was used.

Example 9: Immunofluorescence and Imaging

For immunocytochemistry, Min6 cells were plated in Ibidi (Munich, Germany) 8-well chamber dishes (treated) at a cell density of $5 \times 10^4$ cells/well. Three days after seeding cells were directly fixed with 4% PFA for 10 min followed by a 10 min incubation in permeabilization solution (0.1 M Glycin, 0.2% Triton-X100 in 1×PBS). After blocking (10% donkey serum, 1% BSA and 5% FCS, 0.5% Tween-20 in 1×PBS) for 1 h, cells were incubated in blocking solution containing primary antibodies overnight at 4° C.: IGFR-like receptor Seq ID No. 2 (rat and mouse 1:10), GM130 (1:300, BD, 610822), IGF2R (1:100 ThermoScientific, PA3-850). The following secondary antibodies were applied for 2 h at room temperature in blocking solution: donkey anti-rabbit IgG-555 (1:800, Invitrogen, A31572), donkey anti-mouse IgG-488 (1:800, Invitrogen, A21202), and donkey anti-rat IgG 647 (1:400, Dianova, 712-605-150). After DAPI staining (50 ng/ml), the samples were mounted with elvanol and images were acquired on a Leica laser-scanning SP5 confocal microscope with 63× objective.

For immunohistochemistry in mouse tissue, pancreata were dissected and fixed in 4% PFA in PBS for 2 h at 4° C., cryoprotected in a gradient series of sucrose solutions (7.5, 15 and 30% sucrose in PBS) for at least 2 h in each solution and finally the organs were embedded in Tissue Freezing medium (Leica 14020108926) and stored at −80° C. 20 µm sections were used for immunostaining. Briefly the sections were washed in PBS, permeabilized in 0.1% Triton X-100, 0.1M Glycine in PBS for 15 minutes and then blocked in blocking solution (10% FCS, 3% Donkey serum, 0.1% BSA and 0.1% Tween-20 in PBS) for 1 h at room temperature. Primary antibodies were diluted in blocking solution and incubated over night at 4° C. Next day the sections were washed three times for 5 minutes each in PBST (0.1% Tween-20 in PBS) incubated in secondary antibodies diluted in blocking solution for 3-5 h at room temperature, stained with DAPI (4', 6-diamidin-2-phenylindol) and mounted in embedding medium (ProLong Gold antifade embedding medium, Life Technologies).

For whole-mount staining of the human islets, the islets were fixed in 4% PFA in PBS for 15 min at RT and directly incubated overnight at 4° C. with primary antibodies diluted in blocking solution followed by three washes in PBST and then incubated with secondary antibodies for 3-5 hours at RT as above.

For staining of human tissue sections snap frozen pancreata pieces from human donors were embedded in Tissue Freezing medium (Leica 14020108926) and stored at −80° C. 10 μm thick section sections were fixed in in 4% PFA in PBS for 20 min at RT, washed 2 times with PBS and permeabilized for 5 min on ice. Antibodies staining procedure was performed as described above.

Primary antibodies used were anti-IGFR-like receptor rabbit SEQ ID No 2 1:100, anti-IGFR-like receptor SEQ ID No: 2 and SEQ ID No. 4 rat 1:10, IGFR-like receptor SEQ ID No: 2 and SEQ ID No. 6 mouse 1:10, anti-Insulin (Rabbit 1:250; Cell Signaling; 3014), anti-Insulin (Guinea pig 1:250; Thermo Scientific; PA1-26938), anti-E-Cadherin (Rat 1:500; DECMA Kremmer) anti-Mannose 6P receptor (Rabbit 1:200; Thermo Scientific; PA3-850) and anti-Urocortin 3 (Rabbit 1:300; Phoenix Pharmaceuticals; H-019-29). Secondary antibodies used were Anti-Rabbit Alexa-555 (1:800; Invitrogen; A31572), Anti-Rabbit Alexa-488 (1:800; Invitrogen; A21206), Anti-Rat Alexa-488 (1:800; life technologies, A-21208), Anti-Rat Alexa-647 (1:800; Dianova, 712-605-150) and Anti-Guinea Pig Alexa647 (1:800; Dianova; 706-495-148) Anti-mouse Alexa-555 (1:800; Invitrogen; A31570). Pictures were taken on a Leica DMI 6000 microscope.

Example 10: Immunoprecipitation Assay

For immunoprecipitation assay Min6 cells were starved for 15, 30, 60 and 120 minutes in HBSS with 0.2% BSA fatty acids free and lysed in immunoprecipitation buffer (2% CHAPS, 50 mM HEPES pH 7.5, 200 mM NaCl, 2 mM EDTA) containing a cocktail of proteinase inhibitor (1:100, Sigma, P8340) for 20 minutes on ice. The lysates were cleared by centrifugation for 30 min at 14000 rpm and 4° C. Approximately 500 ug whole cell lysates was incubated with an IGFR-like receptor SEQ ID No 2 antibody generated in rat and diluted 1:10 for 1 h at 4° C. followed by an incubation with protein G Sepharose 4 Fast Flow (GE Healthcare) for 16 h at 4° C. The precipitates were washed 5 times with immunoprecipitation buffer, denatured at 95° C. for 5 min in 2×SDS sample buffer (100 mM Tris-HCL, 4% SDS, 20% glycerol, 0.2% bromphenol blue) containing 100 mM DTT and 5% 2-mercaptoethanol and subjected to Western blot analysis.

Example 11: Surface Biotinylation Assay

Min6 cells were incubated with 2 mM EZ-Link® Sulfo-NHS-LC-Biotin (Thermo Scientific) in PBS pH 8.0 for 10 min at room temperature after which the biotinylation reaction was stopped with 100 mM glycine in PBS. The cells were then washed in ice cold PBS and lysed in RIPA buffer containing a cocktail of proteinase inhibitor. After clearing by centrifugation at 14000 rpm and 4° C. for 30 minutes the supernatants were incubated overnight at 4° C. with NeutrAvidin beads (Thermo Scientiic/Pierce). The next day, after washing 5 times in RIPA buffer, the biotin labeled proteins were eluted from the beads by boiling in 2×SDS sample buffer containing 100 mM DTT and 5% 2-mercaptoethanol and subjected to Western blot analysis.

What is claimed is:

1. An in vitro screening method for antagonists of an IGFR-like receptor 2, said method comprising steps of:
    (a) providing a stable cell line expressing said IGFR-like receptor 2;
    (b) contacting said cell line with a candidate antagonist of the IGFR-like receptor 2; and
    (c) measuring IGFR-like receptor 2 downstream signaling events comprising (i) InsR phosphorylation, (ii) AKT phosphorylation, or both (i) and (ii),
    wherein an antagonist of the IGFR-like receptor 2 is identified if it causes an increase in (i) InsR phosphorylation, (ii) AKT phosphorylation, or both (i) and (ii),
    wherein said IGFR-like receptor 2 comprises a sequence corresponding to sequence SEQ ID NO: 2.

2. The in vitro method of claim 1, wherein said candidate antagonist is selected from an antibody, a siRNA, a nucleic acid, an aptamer, a peptide, a protein, or a small molecule organic compound.

3. The in vitro method of claim 2, wherein said antibody is a monoclonal or polyclonal antibody.

4. The in vitro method of claim 1, wherein said cell line is Min6 cells or PDX1+/NKX6.1+iPSC cells.

5. The in vitro method of claim 1, wherein the measuring of said (i) InsR phosphorylation, (ii) AKT phosphorylation, or both (i) and (ii), of step (c) is compared to (i) InsR phosphorylation, (ii) AKT phosphorylation, or both (i) and (ii), measured in a control cell line that was not contacted with said candidate antagonist.

* * * * *

SEQUENCE LISTING

<160> NUMBER OF SEQ ID NOS: 4

<210> SEQ ID NO 1
<211> LENGTH: 3090
<212> TYPE: DNA
<213> ORGANISM: Homo sapiens

<400> SEQUENCE: 1

```
atgctgttcc gcgcccgggg gccggtacgg ggcaggggct gggggcggcc ggcggaggct      60 cccgccgcg ggcgctcgcc gccctggagc cccgcctgga tttgctgctg ggcgctcgcc     120
ggctgccagg cggcctgggc tggggacctg ccctcctcct ccagccgccc gcttcctcct     180
tgccaggaga aagattatca ctttgaatat acggaatgtg atagcagtgg ctccaggtgg     240
agagttgcca ttccaaattc tgcagtggac tgctctggcc tgcctgaccc agtgagaggc     300
aaagaatgca ctttctcctg tgcttctgga gagtatctag aaatgaagaa ccaggtatgc     360
agtaagtgtg gtgaaggcac ctattccttg ggcagtggca tcaaatttga tgaatgggat     420
gaattgccgc caggattttc taacatcgca acattcatgg acactgtggt gggcccttct     480
gacagcaggc cagacggctg taacaactct tcttggatcc ctcgtggaaa ctacatagaa     540
tctaatcgtg atgactgcac ggtgtctttg atctatgctg tgcaccttaa gaagtcaggc     600
tatgtcttct ttgagtacca gtatgtcgac aacaacatct tctttgagtt ctttattcaa     660
aatgatcagt gccaggagat ggacaccacc actgacaagt gggtaaaact tacagacaat     720
ggagaatggg gctctcattc tgtaatgctg aaatcaggca caaacatact ctactggaga     780
actacaggca tccttatggg ttctaaggcg gtcaagcctg tgctggtaaa aaatatcaca     840
attgaagggg tggcgtacac atcagaatgt tttccttgca agccaggcac attcagcaac     900
```

-continued

```
aaaccaggtt cattcaactg ccaggtgtgt cccagaaaca cctattctga gaaaggagcc    960
aaagaatgta taaggtgtaa agacgactct caattttcag aggaaggatc cagtgagtgt   1020
acagagcgcc ctccctgtac cacaaaagac tatttccaga tccatactcc atgtgatgaa   1080
gaaggaaaga cacagataat gtacaagtgg atagagccca aaatctgccg ggaggatctc   1140
acagatgcta ttagattgcc cccttctgga gagaagaagg attgtccgcc ttgcaaccct   1200 ggatttata caatggatc atcttcttgc catccctgtc ctcctggaac attttcagat   1260
ggaaccaaag aatgtagacc atgtccagca ggaacggagc ctgcacttgg ctttgaatat   1320
aaatggtgga atgtccttcc tggcaacatg aaaacttcct gcttcaatgt tgggaattca   1380
aagtgcgatg gaatgaatgg ttgggaggtg gctggagatc atatccagag tggggctgga   1440
ggttctgaca atgattacct gatcttaaac ttgcatatcc caggatttaa accaccaaca   1500
tctatgactg gagccacggg ttctgaacta ggaagaataa catttgtctt tgagaccctc   1560
tgttcagctg actgtgtttt gtacttcatg gtggatatta atagaaaaag tacaaatgtg   1620
gtagaatcgt ggggtggaac caaagaaaaa caagcttaca cccatatcat cttcaagaat   1680 gcaacttta catttacatg gcattccag agaactaatc agggtcaaga taatagacgg    1740
ttcatcaatg acatggtgaa gatttattct atcacagcca ctaatgcagt tgatggggtg   1800
gcgtcctcat gccgtgcctg tgccctcggt tctgaacagt cgggttcatc gtgtgtcccc   1860
tgccctccag gccactacat tgagaaagaa accaaccagt gcaaggaatg tccacctgac   1920
acctacctgt ccatacatca ggtctatggc aaagaggctt gtattccatg cgggcctggg   1980
agtaaaaaca atcaggacca ttcggtttgc tatagtgact gcttttttcta ccatgaaaaa   2040 gaaaatcaga gtttgcacta tgactttagc aacctcagca gtgtgggctc attaatgaat   2100
ggccccagct tcacctccaa aggaacaaaa tacttccatt tcttcaatat cagtttatgt   2160
gggcatgagg ggaagaagat ggctctctgt accaacaata taacagactt tacagtaaaa   2220
gaaatagtgg cagggtcaga tgattacaca aatttggtag gggcatttgt atgccagtca   2280
acaattattc cttctgaaag taagggtttc cgagcagcct tatcatcaca atccatcatt   2340
ctggcagata cattcatagg agtcacagtt gaaaccacat tgaaaatat taatataaaa    2400 gaagatatgt tcccagttcc aacaagccaa ataccagatg tgcatttctt ttataagtct   2460
tctacagcaa caacatcttg tattaatggc cgatcaactg ctgtgaaaat gaggtgtaat   2520
cctactaaat ctggagcagg agtgatttca gtccccagca gtgcccagc aggtacctgt    2580 gatgggtgta cgttctatt cctgtgggag agtgctgaag cttgccctct gtgtacggag   2640
catgacttcc atgagattga gggagcctgc aagagaggat ttcaggaaac cttgtatgtg   2700
tggaatgaac ctaaatggtg cattaaagga atttcttttgc ctgagaaaaa gttggcaacc   2760
tgtgaaacgg ttgactttg gctgaaggtg ggagccggtg tgggagcttt tactgccgtt   2820
ttgctggtgg ctctgacctg ctacttctgg aaaaagaatc aaaaactgga atacaaatat   2880
tccaagttag taatgacgac taactcaaaa gagtgtgaac tcccggctgc agacagttgt   2940
gctatcatgg aaggagaaga taatgaagag gaagttgtat attccaataa acagtcacta   3000
ctaggaaaac tcaaatcttt ggcaaccaag gaaaagaag accatttga atctgttcaa   3060 ctgaaaacct caagatcccc aaatatatga                                   3090
```

<210> SEQ ID NO 2
<211> LENGTH: 1029
<212> TYPE: PRT

-continued

<213> ORGANISM: Homo sapiens

<400> SEQUENCE: 2

Met Leu Phe Arg Ala Arg Gly Pro Val Arg Gly Gly Trp Gly Arg
1               5                   10                  15

Pro Ala Glu Ala Pro Arg Arg Gly Arg Ser Pro Pro Trp Ser Pro Ala
            20                  25                  30

Trp Ile Cys Cys Trp Ala Leu Ala Gly Cys Gln Ala Ala Trp Ala Gly
        35                  40                  45

Asp Leu Pro Ser Ser Ser Arg Pro Leu Pro Pro Cys Gln Glu Lys
    50                  55                  60

Asp Tyr His Phe Glu Tyr Thr Glu Cys Asp Ser Ser Gly Ser Arg Trp
65                  70                  75                  80

Arg Val Ala Ile Pro Asn Ser Ala Val Asp Cys Ser Gly Leu Pro Asp
                85                  90                  95

Pro Val Arg Gly Lys Glu Cys Thr Phe Ser Cys Ala Ser Gly Glu Tyr
            100                 105                 110

Leu Glu Met Lys Asn Gln Val Cys Ser Lys Cys Gly Glu Gly Thr Tyr
        115                 120                 125

Ser Leu Gly Ser Gly Ile Lys Phe Asp Glu Trp Asp Glu Leu Pro Ala
130                 135                 140

Gly Phe Ser Asn Ile Ala Thr Phe Met Asp Thr Val Gly Pro Ser
145                 150                 155                 160

Asp Ser Arg Pro Asp Gly Cys Asn Asn Ser Ser Trp Ile Pro Arg Gly
                165                 170                 175

Asn Tyr Ile Glu Ser Asn Arg Asp Cys Thr Val Ser Leu Ile Tyr
            180                 185                 190

Ala Val His Leu Lys Lys Ser Gly Tyr Val Phe Phe Glu Tyr Gln Tyr
        195                 200                 205

Val Asp Asn Asn Ile Phe Phe Glu Phe Phe Ile Gln Asn Asp Gln Cys
210                 215                 220

Gln Glu Met Asp Thr Thr Thr Asp Lys Trp Val Lys Leu Thr Asp Asn
225                 230                 235                 240

Gly Glu Trp Gly Ser His Ser Val Met Leu Lys Ser Gly Thr Asn Ile
                245                 250                 255

Leu Tyr Trp Arg Thr Thr Gly Ile Leu Met Gly Ser Lys Ala Val Lys
            260                 265                 270

Pro Val Leu Val Lys Asn Ile Thr Ile Glu Gly Val Ala Tyr Thr Ser
        275                 280                 285

Glu Cys Phe Pro Cys Lys Pro Gly Thr Phe Ser Asn Lys Pro Gly Ser
290                 295                 300

Phe Asn Cys Gln Val Cys Pro Arg Asn Thr Tyr Ser Glu Lys Gly Ala
305                 310                 315                 320

Lys Glu Cys Ile Arg Cys Lys Asp Ser Gln Phe Ser Glu Glu Gly
                325                 330                 335

Ser Ser Glu Cys Thr Glu Arg Pro Pro Cys Thr Thr Lys Asp Tyr Phe
            340                 345                 350

Gln Ile His Thr Pro Cys Asp Glu Glu Gly Lys Thr Gln Ile Met Tyr
        355                 360                 365

Lys Trp Ile Glu Pro Lys Ile Cys Arg Glu Asp Leu Thr Asp Ala Ile
370                 375                 380

Arg Leu Pro Pro Ser Gly Glu Lys Lys Asp Cys Pro Pro Cys Asn Pro
385                 390                 395                 400

-continued

```
Gly Phe Tyr Asn Asn Gly Ser Ser Ser Cys His Pro Cys Pro Pro Gly
                405                 410                 415
Thr Phe Ser Asp Gly Thr Lys Glu Cys Arg Pro Cys Pro Ala Gly Thr
            420                 425                 430
Glu Pro Ala Leu Gly Phe Glu Tyr Lys Trp Trp Asn Val Leu Pro Gly
        435                 440                 445
Asn Met Lys Thr Ser Cys Phe Asn Val Gly Asn Ser Lys Cys Asp Gly
    450                 455                 460
Met Asn Gly Trp Glu Val Ala Gly Asp His Ile Gln Ser Gly Ala Gly
465                 470                 475                 480
Gly Ser Asp Asn Asp Tyr Leu Ile Leu Asn Leu His Ile Pro Gly Phe
                485                 490                 495
Lys Pro Pro Thr Ser Met Thr Gly Ala Thr Gly Ser Glu Leu Gly Arg
            500                 505                 510
Ile Thr Phe Val Phe Glu Thr Leu Cys Ser Ala Asp Cys Val Leu Tyr
        515                 520                 525
Phe Met Val Asp Ile Asn Arg Lys Ser Thr Asn Val Val Glu Ser Trp
    530                 535                 540
Gly Gly Thr Lys Glu Lys Gln Ala Tyr Thr His Ile Ile Phe Lys Asn
545                 550                 555                 560
Ala Thr Phe Thr Phe Thr Trp Ala Phe Gln Arg Thr Asn Gln Gly Gln
                565                 570                 575
Asp Asn Arg Arg Phe Ile Asn Asp Met Val Lys Ile Tyr Ser Ile Thr
            580                 585                 590
Ala Thr Asn Ala Val Asp Gly Val Ala Ser Ser Cys Arg Ala Cys Ala
        595                 600                 605
Leu Gly Ser Glu Gln Ser Gly Ser Ser Cys Val Pro Cys Pro Pro Gly
    610                 615                 620
His Tyr Ile Glu Lys Glu Thr Asn Gln Cys Lys Glu Cys Pro Pro Asp
625                 630                 635                 640
Thr Tyr Leu Ser Ile His Gln Val Tyr Gly Lys Glu Ala Cys Ile Pro
                645                 650                 655
Cys Gly Pro Gly Ser Lys Asn Asn Gln Asp His Ser Val Cys Tyr Ser
            660                 665                 670
Asp Cys Phe Phe Tyr His Glu Lys Glu Asn Gln Ser Leu His Tyr Asp
        675                 680                 685
Phe Ser Asn Leu Ser Ser Val Gly Ser Leu Met Asn Gly Pro Ser Phe
    690                 695                 700
Thr Ser Lys Gly Thr Lys Tyr Phe His Phe Asn Ile Ser Leu Cys
705                 710                 715                 720
Gly His Glu Gly Lys Lys Met Ala Leu Cys Thr Asn Asn Ile Thr Asp
                725                 730                 735
Phe Thr Val Lys Glu Ile Val Ala Gly Ser Asp Asp Tyr Thr Asn Leu
            740                 745                 750
Val Gly Ala Phe Val Cys Gln Ser Thr Ile Ile Pro Ser Glu Ser Lys
        755                 760                 765
Gly Phe Arg Ala Ala Leu Ser Ser Gln Ser Ile Leu Ala Asp Thr
    770                 775                 780
Phe Ile Gly Val Thr Val Glu Thr Thr Leu Lys Asn Ile Asn Ile Lys
785                 790                 795                 800
Glu Asp Met Phe Pro Val Pro Thr Ser Gln Ile Pro Asp Val His Phe
                805                 810                 815
Phe Tyr Lys Ser Ser Thr Ala Thr Thr Ser Cys Ile Asn Gly Arg Ser
```

```
                820                 825                 830
Thr Ala Val Lys Met Arg Cys Asn Pro Thr Lys Ser Gly Ala Gly Val
            835                 840                 845

Ile Ser Val Pro Ser Lys Cys Pro Ala Gly Thr Cys Asp Gly Cys Thr
            850                 855                 860

Phe Tyr Phe Leu Trp Glu Ser Ala Glu Ala Cys Pro Leu Cys Thr Glu
865                 870                 875                 880

His Asp Phe His Glu Ile Glu Gly Ala Cys Arg Gly Phe Gln Glu
                885                 890                 895

Thr Leu Tyr Val Trp Asn Glu Pro Lys Trp Cys Ile Lys Gly Ile Ser
            900                 905                 910

Leu Pro Glu Lys Lys Leu Ala Thr Cys Glu Thr Val Asp Phe Trp Leu
            915                 920                 925

Lys Val Gly Ala Gly Val Gly Ala Phe Thr Ala Val Leu Leu Val Ala
            930                 935                 940

Leu Thr Cys Tyr Phe Trp Lys Lys Asn Gln Lys Leu Glu Tyr Lys Tyr
945                 950                 955                 960

Ser Lys Leu Val Met Thr Thr Asn Ser Lys Glu Cys Glu Leu Pro Ala
                965                 970                 975

Ala Asp Ser Cys Ala Ile Met Glu Gly Glu Asp Asn Glu Glu Val
            980                 985                 990

Val Tyr Ser Asn Lys Gln Ser Leu  Leu Gly Lys Leu Lys  Ser Leu Ala
            995                 1000                1005

Thr Lys  Glu Lys Glu Asp His  Phe Glu Ser Val Gln  Leu Lys Thr
    1010                1015                1020

Ser Arg  Ser Pro Asn Ile
    1025

<210> SEQ ID NO 3
<211> LENGTH: 3042
<212> TYPE: DNA
<213> ORGANISM: Homo sapiens

<400> SEQUENCE: 3
atggctgagc ctgggcacag ccaccatctc tccgccagag tcaggggaag aactgagagg    60 cgcataccc ggctgtggcg gctgctgctc tgggctggga ccgccttcca ggtgacccag    120
ggaacgggac cggagcttca tgcctgcaaa gagtctgagt accactatga gtacacggcg    180
tgtgacagca cgggttccag gtggagggtc gccgtgccgc ataccccggg cctgtgcacc    240
agcctgcctg accccatcaa gggcaccgag tgctccttct cctgcaacgc cggggagttt    300
ctggatatga aggaccagtc atgtaagcca tgcgctgagg ccgctactc cctcggcaca    360 ggcattcggt tgatgagtg ggatgagctg cccatggct tgccagcct ctcagccaac    420 atggagctgg atgacagtgc tgctgagtcc accgggaact gtacttcgtc caagtgggtt    480
ccccggggcg actacatcgc ctccaacacg gacgaatgca gccacact gatgtacgcc    540 gtcaacctga gcaatctgg caccgttaac ttcgaatact actatccaga ctccagcatc    600
atctttgagt ttttcgttca gaatgaccag tgccagccca tgcagatga ctccaggtgg    660 atgaagacca cagagaaagg atgggaattc cacagtgtgg agctaaatcg aggcaataat    720
gtcctctatt ggagaaccac agccttctca gtatggacca agtacccaa gcctgtgctg    780 gtgagaaaca ttgccataac aggggtggcc tacacttcag aatgcttccc ctgcaaacct    840
ggcacgtatg cagacaagca gggctcctct ttctgcaaac tttgcccagc caactcttat    900
```

-continued

```
tcaaataaag gagaaacttc ttgccaccag tgtgaccctg acaaatactc agagaaagga    960
tcttcttcct gtaacgtgcg cccagcttgc acagacaaag attatttcta cacacacacg   1020
gcctgcgatg ccaacggaga gacacaactc atgtacaaat gggccaagcc gaaaatctgt   1080
agcgaggacc ttgaggggc agtgaagctg cctgcctctg tgtgaagac ccactgccca   1140
ccctgcaacc caggcttctt caaaaccaac aacagcacct gccagccctg cccatatggt   1200
tcctactcca atggctcaga ctgtacccgc tgccctgcag ggactgaacc tgctgtggga   1260
tttgaataca atggtggaa cacgctgccc acaaacatgg aaacgaccgt tctcagtggg   1320
atcaacttcg agtacaaggg catgacaggc tgggaggtgg ctggtgatca catttacaca   1380
gctgctggag cctcagacaa tgacttcatg attctcactc tggttgtgcc aggatttaga   1440
cctccgcagt cggtgatggc agacacagag aataaagagg tggccagaat cacatttgtc   1500
tttgagaccc tctgttctgt gaactgtgag ctctacttca tggtgggtgt gaattctagg   1560
accaacactc ctgtggagac gtggaaaggt tccaaaggca acagtcctaa cctacatc   1620
attgaggaga acactaccac gagcttcacc tgggccttcc agaggaccac ttttcatgag   1680
gcaagcagga agtacaccaa tgacgttgcc aagatctact ccatcaatgt caccaatgtt   1740
atgaatggtg tggcctccta ctgccgtccc tgtgccctag aagcctctga tgtgggctcc   1800
tcctgcacct cttgtcctgc tggttactat attgaccgag attcaggaac ctgccactcc   1860
tgccccacta acacaattct gaaagcccac cagcctatg gtgtccaggc ctgtgtgccc   1920
tgtggtccag ggaccaagaa caacaagatc cactctctgt gctacaacga ttgcaccttc   1980
tcacgcaaca ctccgaccag gactttcaac tacaacttct ccgctttggc aaacactgtc   2040
actcttgctg gagggccaag cttcacttcc aaagggctga atacttcca tcactttacc   2100
ctcagtctct gtggaaacca gggtaggaaa atgtctgtgt gcaccgacaa tgtcactgac   2160
ctccggattc ctgagggtga gtcagggttc tccaaatcta tcacagccta cgtctgccag   2220
gcagtcatca tcccccaga ggtgacaggc tacaaggccg gggtttcctc acagcctgtc   2280
agccttgctg atcgacttat tggggtgaca acagatatga ctctggatgg aatcacctcc   2340
ccagctgaac ttttccacct ggagtccttg gaataccgg acgtgatctt cttttatagg   2400
tccaatgatg tgacccagtc ctgcagttct gggagatcaa ccaccatccg cgtcaggtgc   2460
agtccacaga aaactgtccc tggaagtttg ctgctgccag aacgtgctc ggatgggacc   2520
tgtgatggct gcaacttcca cttcctgtgg gagagcgcgg ctgcttgccc gctctgctca   2580
gtggctgact accatgctat cgtcagcagc tgtgtggctg ggatccagaa gactacttac   2640
gtgtggcgag aacccaagct atgctctggt ggcatttctc tgcctgagca gagagtcacc   2700
atctgcaaaa ccatagattt ctggctgaaa gtgggcatct ctgcaggcac ctgtactgcc   2760
atcctgctca ccgtcttgac ctgctacttt tggaaaaaga atcaaaaact agagtacaag   2820
tactccaagc tggtgatgaa tgctactctc aaggactgtg acctgccagc agctgacagc   2880
tgcgccatca tggaaggcga ggatgtagag gacgacctca tctttaccag caagaagtca   2940
ctctttggga agatcaaatc atttacctcc aagaggactc ctgatggatt tgactcagtg   3000
ccgctgaaga catcctcagg aggcctagac atggacctgt ga                      3042
```

<210> SEQ ID NO 4
<211> LENGTH: 1013
<212> TYPE: PRT
<213> ORGANISM: Homo sapiens

<400> SEQUENCE: 4

```
Met Ala Glu Pro Gly His Ser His His Leu Ser Ala Arg Val Arg Gly
1               5                   10                  15

Arg Thr Glu Arg Arg Ile Pro Arg Leu Trp Arg Leu Leu Leu Trp Ala
                20                  25                  30

Gly Thr Ala Phe Gln Val Thr Gln Gly Thr Gly Pro Glu Leu His Ala
                35                  40                  45

Cys Lys Glu Ser Glu Tyr His Tyr Glu Tyr Thr Ala Cys Asp Ser Thr
            50                  55                  60

Gly Ser Arg Trp Arg Val Ala Val Pro His Thr Pro Gly Leu Cys Thr
65                  70                  75                  80

Ser Leu Pro Asp Pro Ile Lys Gly Thr Glu Cys Ser Phe Ser Cys Asn
                85                  90                  95

Ala Gly Glu Phe Leu Asp Met Lys Asp Gln Ser Cys Lys Pro Cys Ala
                100                 105                 110

Glu Gly Arg Tyr Ser Leu Gly Thr Gly Ile Arg Phe Asp Glu Trp Asp
            115                 120                 125

Glu Leu Pro His Gly Phe Ala Ser Leu Ser Ala Asn Met Glu Leu Asp
            130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
                180                 185                 190

Tyr Tyr Tyr Pro Asp Ser Ser Ile Ile Phe Glu Phe Val Gln Asn
            195                 200                 205

Asp Gln Cys Gln Pro Asn Ala Asp Asp Ser Arg Trp Met Lys Thr Thr
            210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
                260                 265                 270

Ser Glu Cys Phe Pro Cys Lys Pro Gly Thr Tyr Ala Asp Lys Gln Gly
            275                 280                 285

Ser Ser Phe Cys Lys Leu Cys Pro Ala Asn Ser Tyr Ser Asn Lys Gly
            290                 295                 300

Glu Thr Ser Cys His Gln Cys Asp Pro Asp Lys Tyr Ser Glu Lys Gly
305                 310                 315                 320

Ser Ser Ser Cys Asn Val Arg Pro Ala Cys Thr Asp Lys Asp Tyr Phe
                325                 330                 335

Tyr Thr His Thr Ala Cys Asp Ala Asn Gly Glu Thr Gln Leu Met Tyr
                340                 345                 350

Lys Trp Ala Lys Pro Lys Ile Cys Ser Glu Asp Leu Glu Gly Ala Val
            355                 360                 365

Lys Leu Pro Ala Ser Gly Val Lys Thr His Cys Pro Pro Cys Asn Pro
            370                 375                 380

Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
                405                 410                 415
```

```
Pro Ala Val Gly Phe Glu Tyr Lys Trp Trp Asn Thr Leu Pro Thr Asn
                420                 425                 430
Met Glu Thr Thr Val Leu Ser Gly Ile Asn Phe Glu Tyr Lys Gly Met
            435                 440                 445
Thr Gly Trp Glu Val Ala Gly Asp His Ile Tyr Thr Ala Ala Gly Ala
        450                 455                 460
Ser Asp Asn Asp Phe Met Ile Leu Thr Leu Val Val Pro Gly Phe Arg
465                 470                 475                 480
Pro Pro Gln Ser Val Met Ala Asp Thr Glu Asn Lys Glu Val Ala Arg
                485                 490                 495
Ile Thr Phe Val Phe Glu Thr Leu Cys Ser Val Asn Cys Glu Leu Tyr
            500                 505                 510
Phe Met Val Gly Val Asn Ser Arg Thr Asn Thr Pro Val Glu Thr Trp
        515                 520                 525
Lys Gly Ser Lys Gly Lys Gln Ser Tyr Thr Tyr Ile Ile Glu Glu Asn
            530                 535                 540
Thr Thr Thr Ser Phe Thr Trp Ala Phe Gln Arg Thr Thr Phe His Glu
545                 550                 555                 560
Ala Ser Arg Lys Tyr Thr Asn Asp Val Ala Lys Ile Tyr Ser Ile Asn
                565                 570                 575
Val Thr Asn Val Met Asn Gly Val Ala Ser Tyr Cys Arg Pro Cys Ala
            580                 585                 590
Leu Glu Ala Ser Asp Val Gly Ser Cys Thr Ser Cys Pro Ala Gly
        595                 600                 605
Tyr Tyr Ile Asp Arg Asp Ser Gly Thr Cys His Ser Cys Pro Thr Asn
610                 615                 620
Thr Ile Leu Lys Ala His Gln Pro Tyr Gly Val Gln Ala Cys Val Pro
625                 630                 635                 640
Cys Gly Pro Gly Thr Lys Asn Asn Lys Ile His Ser Leu Cys Tyr Asn
                645                 650                 655
Asp Cys Thr Phe Ser Arg Asn Thr Pro Thr Arg Thr Phe Asn Tyr Asn
            660                 665                 670
Phe Ser Ala Leu Ala Asn Thr Val Thr Leu Ala Gly Gly Pro Ser Phe
        675                 680                 685
Thr Ser Lys Gly Leu Lys Tyr Phe His His Phe Thr Leu Ser Leu Cys
        690                 695                 700
Gly Asn Gln Gly Arg Lys Met Ser Val Cys Thr Asp Asn Val Thr Asp
705                 710                 715                 720
Leu Arg Ile Pro Glu Gly Glu Ser Gly Phe Ser Lys Ser Ile Thr Ala
                725                 730                 735
Tyr Val Cys Gln Ala Val Ile Ile Pro Pro Glu Val Thr Gly Tyr Lys
            740                 745                 750
Ala Gly Val Ser Ser Gln Pro Val Ser Leu Ala Asp Arg Leu Ile Gly
        755                 760                 765
Val Thr Thr Asp Met Thr Leu Asp Gly Ile Thr Ser Pro Ala Glu Leu
770                 775                 780
Phe His Leu Glu Ser Leu Gly Ile Pro Asp Val Ile Phe Phe Tyr Arg
785                 790                 795                 800
Ser Asn Asp Val Thr Gln Ser Cys Ser Ser Gly Arg Ser Thr Thr Ile
                805                 810                 815
Arg Val Arg Cys Ser Pro Gln Lys Thr Val Pro Gly Ser Leu Leu Leu
            820                 825                 830
Pro Gly Thr Cys Ser Asp Gly Thr Cys Asp Gly Cys Asn Phe His Phe
```

-continued

```
                835                 840                 845
Leu Trp Glu Ser Ala Ala Ala Cys Pro Leu Cys Ser Val Ala Asp Tyr
    850                 855                 860

His Ala Ile Val Ser Ser Cys Val Ala Gly Ile Gln Lys Thr Thr Tyr
865                 870                 875                 880

Val Trp Arg Glu Pro Lys Leu Cys Ser Gly Gly Ile Ser Leu Pro Glu
                885                 890                 895

Gln Arg Val Thr Ile Cys Lys Thr Ile Asp Phe Trp Leu Lys Val Gly
            900                 905                 910

Ile Ser Ala Gly Thr Cys Thr Ala Ile Leu Leu Thr Val Leu Thr Cys
        915                 920                 925

Tyr Phe Trp Lys Lys Asn Gln Lys Leu Glu Tyr Lys Tyr Ser Lys Leu
    930                 935                 940

Val Met Asn Ala Thr Leu Lys Asp Cys Asp Leu Pro Ala Ala Asp Ser
945                 950                 955                 960

Cys Ala Ile Met Glu Gly Glu Asp Val Glu Asp Asp Leu Ile Phe Thr
                965                 970                 975

Ser Lys Lys Ser Leu Phe Gly Lys Ile Lys Ser Phe Thr Ser Lys Arg
            980                 985                 990

Thr Pro Asp Gly Phe Asp Ser Val  Pro Leu Lys Thr Ser  Ser Gly Gly
        995                 1000                1005

Leu Asp Met Asp Leu
    1010
```